United States Patent
Dhanoa et al.

(10) Patent No.: US 6,518,266 B1
(45) Date of Patent: Feb. 11, 2003

(54) 1-ARYL-3-THIOALKYL PYRAZOLES, THE SYNTHESIS THEREOF AND THE USE THEREOF AS INSECTICIDES

(75) Inventors: Daljit S. Dhanoa, Del Mar, CA (US); Dario Doller, Branford, CT (US); Sanath Meegalla, Devon, PA (US); Richard M. Soll, Lawenceville, NJ (US); Nancy Wisnewski, Fort Collins, CO (US); Gary Silver, Bothell, WA (US); Dan T. Stinchcomb, Fort Collins, CO (US); R. Lee Seward, Eaton, CO (US); Dimitris Agrafiotis, Downingtown, PA (US); Deyou Sha, Yardley, PA (US)

(73) Assignees: 3-Dimensional Pharmaceuticals, Exton, PA (US); Heska Corporation, Fort Collins, CO (US)

( * ) Notice: Subject to any disclaimer, the term of this patent is extended or adjusted under 35 U.S.C. 154(b) by 0 days.

(21) Appl. No.: 09/621,456

(22) Filed: Jul. 21, 2000

Related U.S. Application Data

(60) Provisional application No. 60/145,133, filed on Jul. 22, 1999.

(51) Int. Cl.$^7$ .................... C07D 231/24; C07D 231/16; C07D 231/38; C07D 231/18; A01N 43/56
(52) U.S. Cl. ............... 514/229.2; 548/371; 548/369.7; 548/370.4; 548/377.1; 548/364.1; 548/202; 548/124; 548/110; 548/247; 546/275.4; 546/138; 546/135; 546/144; 544/66; 544/67; 544/333; 544/405; 514/404; 514/403; 514/255.05
(58) Field of Search ................. 548/371, 1, 369.2, 548/370.4, 377.1, 364.1, 202, 247, 124, 110; 544/66, 67, 333, 405; 514/404, 255.05, 229.2, 403; 546/275.4, 138, 144, 135

(56) References Cited

U.S. PATENT DOCUMENTS

| | | | |
|---|---|---|---|
| 1,685,407 A | 9/1928 | Mannich | |
| 3,235,360 A | 2/1966 | Soboczenski | 71/2.5 |
| 3,326,662 A | 6/1967 | Toyosato et al. | 71/2.5 |
| 3,364,227 A | 1/1968 | Robinson | 260/310 |
| 3,637,738 A | 1/1972 | Gschwend et al. | 260/311 |
| 3,818,026 A | 6/1974 | Boesch | 260/307 A |
| 3,836,539 A | 9/1974 | Boesch | 260/307 A |
| 3,846,440 A | 11/1974 | Boesch et al. | 260/307 A |
| 3,883,550 A | 5/1975 | Goddard | 260/310 C |
| 4,059,434 A | 11/1977 | Wolf | 71/92 |
| 4,108,628 A | 8/1978 | Wolf | 71/92 |
| 4,111,681 A | 9/1978 | Goddard | 71/92 |
| 4,124,373 A | 11/1978 | Wolf | 71/92 |
| 4,331,678 A | 5/1982 | De'Ath et al. | 424/273 |
| 4,666,507 A | 5/1987 | Yanagi et al. | 71/92 |
| 4,695,312 A | 9/1987 | Hayase et al. | 71/92 |
| 4,740,231 A | 4/1988 | Gehring et al. | 71/92 |
| 5,104,994 A | 4/1992 | Roberts et al. | 548/376 |
| 5,134,155 A | 7/1992 | Connolly et al. | 514/403 |
| 5,232,940 A | 8/1993 | Hatton et al. | 514/407 |
| 5,306,694 A | 4/1994 | Phillips et al. | 504/253 |
| 5,387,693 A | 2/1995 | Connolly et al. | 548/360.1 |
| 5,487,976 A | 1/1996 | Soderlund et al. | 435/7.21 |
| 5,637,607 A | 6/1997 | Pilato et al. | 514/404 |
| 5,707,936 A | 1/1998 | Oberdorf et al. | 504/253 |
| 5,814,652 A | 9/1998 | Wu | 514/404 |
| 5,849,778 A | 12/1998 | Heil et al. | 514/403 |
| 5,869,517 A | 2/1999 | Müller et al. | 514/407 |
| 6,069,157 A | 5/2000 | Banks | 514/341 |

FOREIGN PATENT DOCUMENTS

DE  19511269 A1  10/1995

(List continued on next page.)

OTHER PUBLICATIONS

A. M Hose et al. Trends in Neurosciences, vol. 20 (12), pp. 578–583, 1997.*

(List continued on next page.)

Primary Examiner—Mark L. Berch
Assistant Examiner—Kahsay Habte
(74) Attorney, Agent, or Firm—Sterne, Kessler, Goldstein & Fox PLLC

(57) ABSTRACT

The present invention is directed to novel pyrazole derivatives and their use as pesticidal agents. The pyrazole derivatives have Formula I:

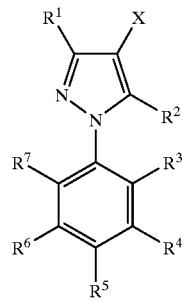

or a salt thereof, where $R^1$ represents $R^5O$, $R^5SO_2$, $R^5SO$ or $R^5S$ in which $R^5$ is as defined herein;

X is halo, cyano, $C_{1-6}$ alkoxycarbonyl, $C_{2-6}$ alkynyl, optionally substituted $C_{6-14}$ aryl or an optionally substituted 5- to 7-membered heteroaromatic ring linked to thiazole via a carbon-carbon bond;

$R^2$ is hydrogen, amino, chloro, bromo, iodo, cyano, $C_{1-6}$ alkoxy, $C_{1-6}$ alkyl or $C_{6-10}$ aryl; and $R^3$–$R^7$ each represent hydrogen, halogen, straight- or branched-chain $C_{1-4}$ alkyl or $C_{1-4}$ alkoxy, either of which is unsubstituted or substituted by one or more halogen atoms, straight- or branched-chain $C_{1-4}$ alkylthio or $C_{1-4}$ alkylsulphinyl, either of which is substituted by one or more halogen atoms, nitro, cyano, or straight- or branched-chain $C_{1-4}$ alkylsulphonyl group which is unsubstituted or substituted by one or more halogen atoms.

41 Claims, No Drawings

FOREIGN PATENT DOCUMENTS

| | | |
|---|---|---|
| DE | 19518054 A1 | 9/1996 |
| DE | 19544799 A1 | 6/1997 |
| DE | 197 56 115 A1 | 6/1999 |
| EP | 0 350 311 A1 | 1/1990 |
| EP | 0 398 499 A2 | 11/1990 |
| EP | 0 412 849 A2 | 2/1991 |
| EP | 0 418 016 A1 | 3/1991 |
| EP | 0 558 999 A2 | 9/1993 |
| EP | 0 659 745 A1 | 6/1995 |
| EP | 0 152 286 A1 | 8/1995 |
| EP | 0 745 684 A1 | 12/1996 |
| EP | 0 234 119 A1 | 9/1997 |
| EP | 0 846 686 A1 | 6/1998 |
| FR | 2301250 | 10/1976 |
| FR | 0 138 527 A2 | 4/1985 |
| JP | 59181259 | 10/1984 |
| JP | 6041667 | 3/1985 |
| JP | 60-233061 | 11/1985 |
| JP | 61-165373 | 7/1986 |
| JP | 63-287766 | 11/1988 |
| JP | 8208620 | 8/1996 |
| KR | 917886 | 10/1991 |
| WO | WO 92/13451 | 8/1992 |
| WO | WO 93/06089 | 4/1993 |
| WO | WO 93/19054 | 9/1993 |
| WO | WO 93/21160 | 10/1993 |
| WO | WO 94/13643 | 6/1994 |
| WO | WO 94/13644 | 6/1994 |
| WO | WO 94/13661 | 6/1994 |
| WO | WO 94/13677 | 6/1994 |
| WO | WO 94/21606 | 9/1994 |
| WO | WO 95/22530 | 8/1995 |
| WO | WO 95/33727 | 12/1995 |
| WO | WO 98/22442 A2 | 5/1998 |

OTHER PUBLICATIONS

Cole, L.M. et al., "Action of Phenylpyrazole Insecticides at the GABA–Gated Chloride Channel," *Pesticide Biochem. Physiol.* 46:47–54 Academic Press, New York, NY (1993).

Finkelstein, B.L. and C.J. Strock, "Synthesis and Insecticidal Activity of Novel Pyrazole Methanesulfonates," *Pestic. Sci.* 50:324–328 John Wiley & Sons, New York, NY (1997).

Dialog File 351, Accession No. 4146500, Derwent WPI English language abstract for JP 59181259 (Document AL1).

Dialog File 351, Accession No. 4264102, Derwent WPI English language abstract for JP 6041667 (Document AM1).

Dialog File 351, Accession No. 9260868, Derwent WPI English language absract for KR 917886 (Document AN2).

Dialog File 351, Accession No. 10324917, Derwent WPI English language abstract for EP 0 659 745 A1 (Document AL4).

Dialog File 351, Accession No. 10392384, Derwent WPI English language abstract for WO 95/22530 (Document AM4).

Dialog File 351, Accession No. 10451076, Derwent WPI English language abstract for DE 19511269 A1 (Document AN4).

Dialog File 351, Accession No. 10925014, Derwent WPI English language abstract for JP 8208620 (Document AO4).

Dialog File 351, Accession No. 10916684, Derwent WPI English language abstract for DE 19518054 A1 (Document AP4).

Dialog File 351, Accession No. 11321362, Derwent WPI English language abstract for DE 19544799 A1 (Document AL5).

Ando, I. et al., "Synthesis and Biological Activity of Cyclic Imide Derivatives and Related Compounds," *Agric. Biol. Chem.* 53:2001–2003, Japan Society for Bioscience, Biotechnology and Agrochemistry, Japan (1989).

Baraldi, P. G. et al., "A Mild One–Pot Synthesis of Thieno [3,4–c]pyrazoles and Their Conversion into Pyrazole Analogs of o–Quinodimethane," *Synthesis* (9):1331–1334, Thieme, New York, NY (Sep. 1998).

Bardou, L. et al., "XVI.—Pyrazoles bicycliques," *Bulletin de la Société Chimique de France* (1):289–294, Société Chimique de France, Paris, France (1967).

Bauer, V.J. et al., "Synthesis, Alkylation, and Oxidation of Thieno[3,4–c]– and —[3,2–c]pyrazoles," *J. Med. Chem.* 14:454–456, American Chemical Society, Washington, DC (1971).

Chou, T.–s. and Chang, R.–C., "A Novel Route to the Preparation of Pyrazole Analogues of o–Xylylene," *J. Org. Chem.* 58:493–496, American Chemical Society, Washington, DC (1993).

Chou, T.–s. and Chang, R.–C., "Synthesis and Reactions of N–Substituted Pyrazolo–3–Sulfolenes," *Heterocycles* 36:2839–2850, Elsevier Science, New York, NY (1993).

Connolly, P.J. et al., "HMG–CoA Reductase Inhibitors: Design, Synthesis, and Biological Activity of Tetrahydroindazole–Substituted 3,5–Dihydroxy–6–heptenoic Acid Sodium Salts," *J. Med. Chem.* 36:3674–3685, American Chemical Society, Washington, DC (1993).

Duncan, D.C. et al., "The Preparation of N–Carboalkoxypyrazoles and N–Phenylpyrazoles from C(α)–Dianions of Carboalkoxyhydrazones and Phenylhydrazones," *J. Heterocyclic Chem.* 24:555–559, Hetero Corporation, Provo, Utah (1987).

Elguero, J. et al., "XIV.—Étude UV de pyrazoles," *Bulletin de la Société Chimique de France* (12):3744–3752, Société Chimique de France, Paris, France (1966).

Jacquier, R. and Maury, G., "Dinitro–2', 4' phényl)–1 pyrazoles dérivant de 1'hydroxyméthylène–2 cycloheptanone et de l'hydroxyméthylène–3 camphre (Note de Laboratoire)," *Bulletin de la Société Chimique de France* (1):295–297, Société Chimique de France, Paris, France (1967).

pg,11

Jacquier, R. and Maury, G., "XVII.—Synthèses et étude des (dinitro–2',4' phényl)–1 pyrazoles isomères dérivant d'acétyl–2 cyclanones (Première partie)," *Bulletin de la Société Chimique de France* (1):306–315, Société Chimique de France, Paris, France (1967).

Jacquier, R. and Maury, G., "XIX.—Synthèses et étude des (dinitro–2',4' phényl)—1 pyrazoles isomères dérivant d' acétyl–2 cyclanones (Deuxième partie)," *Bulletin de la Société Chimique de France* (1):316–320, Société Chimique de France, Paris, France (1967).

Lyga, J.W. et al., "Synthesis, Mechanism of Action, and QSAR of Herbicidal 3–Substituted–2–aryl–4,5,6,7–tetrahyroindazoles," *Pestic. Sci* 42:29–36, John Wiley & Sons, Inc., New York, NY (1994).

Malik, O.P. et al., "Synthesis of 2,3–Substituted 4,5,6, 7–Tetrahydro–2H–Indazoles; 2,4,5,6,7,8–Hexahydrocyclohepta(C) Pyrazoles and Their ω–t–Aminoalkyl Enol Ethers," *Harayana agric. Univ. J. Res.* 10:218–221 (1980).

Schenone, S. et al., "2–Aryl–3–Phenylamino–4,5–Dihydro–2H–Benz[g] indazoles with Antiarrhythmic and Local Anaesthetic Activities," *Il Farmaco 50*:179–182, Società Chimica Italiana, Rome, Italy (1995).

Strakova, I.A. et al., "Synthesis and Reactions of 1–(2–Pyridyl)–3–Methyl–4–Chloro–5–Formyl–6,7–Dihydroindazoles," *Chem. Heterocyclic Compounds 34*:669–673, Plenum Publishing Corporation, London, England (1988).

Wang, Q. et al., "On the Reaction of 1–Aza–2–azoniaallene Salts with Acetylenes," *Chem. Ber. 127*:541–547, VCH Verlagsgesellschaft mbH, Weinheim, Germany (1994).

Williams, R.P. et al., "Synthesis and Alkylation of Tetrahydrocyclopentapyrazolols," *J. Med. Chem. 13*:773–775, American Chemical Society, Washington, DC (1970).

Yoichi, I., "Phenylpyrazole Derivative and Noxious Life Controlling Agent," *Patent Abstracts of Japan*, Publication No. 05262741, European Patent Office (1993).

Yukiaki, M., "Aminopyrazole Derivative, Its Production and Use," *Patent Abstracts of Japan*, Publication No. 08208620, European Patent Office (1996).

Yikiaki, M., "Pyrazole Derivative, Its Use," *Patent Abstracts of Japan*, Publication No. 08311036, European Patent Office (1996).

Dialog File 351, Accession No. 1662172, Derwent WPI English language abstract for FR 2,301,250 (Document AO5).

CAPLUS Accession No. 1967:473550, Document No. 67:73550, CAPLUS English language abstract, American Chemical Society, Washington, DC, for Document AS5, Bardou, L. et al., *Bulletin de la Société Chimique de France* (1):289–294, Société Chimique de France, Paris, France (1967).

Dialog File 351, Accession No. 4501508, Derwent WPI English language abstract for JP 60–233061 (Document AM6).

Dialog File 351, Accession No. 4732434, Derwent WPI English language abstract for JP 61–165373 (Document AN6).

Dialog File 351, Accession No. 7746781, Derwent WPI English language abstract for JP 63–287766 (Document AO6).

Dialog File 351, Accession No. 9588344, Derwent WPI English language abstract for EP 0 558 999 A2 (Document AP6).

CAPLUS Accession No. 1967:80664, Document No. 66:80664, CAPLUS English language abstract, American Chemical Society, Washington, DC, for Document AS7, Elguero, J. et al., *Bulletin de la Société Chimique de France* 912):3744–3752, Société Chimique de France, Paris, France (1966).

CAPLUS Accession No. 1967:403028, Document No. 67:3028, CAPLUS English language abstract, American Chemical Society, Washington, DC, for Document AT7, Jacquier, R. and Maury, G., *Bulletin de la Société Chimique de France* (1):295–297, Société Chimique de France, Paris, France (1967).

CAPLUS Accession No. 1967:508588, Document No. 67:108588, CAPLUS English language abstract, American Chemical Society, Washington, DC, for Document AR8, Jacquier, R. and Maury, G., *Bulletin de la Société Chimique de France* (1):306–315, Société Chimique de France, Paris, France (1967).

CAPLUS Accession No. 1967:473551, Document No. 67:73551, CAPLUS English lanugage abstract, American Chemical Society, Washington, DC, for Document AS8, Jacquier, R. and Maury, G., *Bulletin de la Société Chimique de France* (1):316–320, SociétéChimique de France, Paris, France (1967).

Dialog File 351, Accession No. 12565980, Derwent WPI English language abstract for DE 197 56 115 A1 (Document AL8).

* cited by examiner

1-ARYL-3-THIOALKYL PYRAZOLES, THE SYNTHESIS THEREOF AND THE USE THEREOF AS INSECTICIDES

This application claims benefit under 35 U.S.C. §119(e) of U.S. Provisional Application No. 60/145,133, filed Jul. 22, 1999, which application is herein incorporated by reference in its entirety.

BACKGROUND OF THE INVENTION

1. Field of the Invention

The present invention is in the field of substituted 1-arylpyrazole compounds, their synthesis and their use as pest GABA receptor inhibitors and pesticides.

2. Related Art

γ-Aminobutyric acid (GABA) receptors are intrinsic membrane glycoproteins in vertebrate and invertebrate neuronal tissues that are members of the ligand-gated ion channel superfamily of receptors. GABA receptors play a major role in the inhibition of central nervous system (CNS) neuronal activity due to the widespread distribution of GABA-releasing and GABA-receptive neurons.

Vertebrate GABA receptors can be divided into two major classes: the $GABA_A$ and $GABA_C$ subtypes, and $GABA_B$ receptor subtype, which are distinguished by differences in their effector mechanisms and pharmacology (Knapp, R. J., et al., Neurochem. Res. 15:105–112 (1990)). $GABA_A$ and $GABA_C$ receptors are transmitter-operated chloride channels that are activated by GABA to open their chloride channel while $GABA_B$ receptors are thought to mediate changes in cyclic AMP levels through the activation of phospholipase activity (Eldefrawi, A. T. and Eldefrawi, M. E., FASEB J. 1:262–271 (1987); Knapp, R. J., et al, Neurochem. Res. 15:105–112 (1990)). The $GABA_A$ receptor and its associated chloride ion channel make up the so-called $GABA_A$ receptor-channel complex.

GABA is the endogenous ligand for the $GABA_A$ receptor of the $GABA_A$-complex, and is the major inhibitory neurotransmitter in the vertebrate brain, in the insect CNS and at insect neuromuscular junctions (Enna et al., In: Benzodiazepine/GABA Receptors and Chloride Channels: Structural and Functional Properties, Alan R. Liss, Inc., New York, pp. 41–56 (1986); Sattelle, D.B., Adv. Insect Physiol. 22:1–113 (1990)). GABA binding to its receptor stimulates chloride ion conductance through the associated chloride ion channel to inhibit synaptic transmission (Knapp, R. J., et al., Neurochem. Res. 15:105–112 (1990); U.S. Pat. No. 5,487,976). When two molecules of GABA bind at sites on the receptor, the chloride channel undergoes a conformational change and opens, allowing chloride ions to flow passively down the electrochemical gradient into the neuron. An influx of chloride into the cell causes a change in the membrane potential, usually a hyperpolarization, which results in an inhibition of the nerve impulse. Blockage of the GABA-gated chloride channel reduces neuronal inhibition, which leads to hyper-excitation of the CNS, resulting in convulsions and death. In contrast, irreversible or hyperactivation of the channel suppresses neuronal activity, resulting in ataxia, paralysis, coma and death (Bloomquist, J. R., Comp. Biochem. Physiol. 106C:301–314 (1993)).

$GABA_A$ receptors belong to the class 1 family of neurotransmitter/hormone receptors. Other class 1 members include the glycine receptor, the serotonin type-3 receptor, the nicotinic acetylcholine receptors (muscle and neuronal types) and several excitatory amino acid receptors of vertebrates. Class 1 receptors employ no second messengers and are found where a fast conductance is required. In contrast to class 1 receptors, class 2 receptors (e.g. muscarinic, adrenergic, and others) are coupled to a second messenger and/or a G protein for their transduction, with the channel involved being separate (and usually distant) from the receptor, which is both an agonist-binding and G protein-binding molecule (Barnard, E. A., et al., TiNS 10:502–509 (1987)).

$GABA_A$ receptors are pentameric oligomers, of about 250 kilodaltons (kDa), composed of six different types of subunits, α, β, γ, δ, ε and ρ, each of approximately 50 kDa (Olsen, R. W., and Tobin, A. J., FASEB J. 4:1469–1480 (1990); Hevers, W., and Lüddens, H., Mol. Neurobiol. 18:35–86 (1998)). Each subunit comprises a large extracellular N-terminal domain that putatively includes the ligand-binding site, four hydrophobic presumed membrane-spanning domains, one or more of which contribute to the wall of the ion channel, and a small extracellular C-terminus (Lüddens, H., and Wisden, W., TiPS 12:49–51 (1991); Olsen, R. W., and Tobin, A. J., FASEB J. 4:1469–1480 (1990); Hevers, W., and Lüddens, H., Mol. Neurobiol. 18:35–86 (1998)). Heterologous expression in vitro of different combinations of GABA receptor subunit types (α, β, γ, δ etc.) and subunit isoforms (α1, α2, etc. except δ) results in heteromultimeric receptors with differing structure and pharmacology (Schofield, P. R., TiPS 10:476–478 (1989); Burt et al., FASEB J. 5:2916–2923 (1991)).

GABA receptors also play an important role in the chemical control of pests, particularly insects, such as fleas, ticks, house flies, fruit flies, plant bugs, boll weevils, grasshoppers, cockroaches, mosquitoes, beetles, locust and moths (Hainzl, D., et al., Chem. Res. Toxicol. 11:1529–1535 (1998)). To date, all insect GABA receptors studied gate a fast acting chloride ion conductance. Although they appear to share many of the properties of $GABA_A$-type receptors in the vertebrate CNS, the majority of receptors in the insect nervous system appear to be bicuculline-, pitrazepin- and RU5135-insensitive (Anthony, N. M., et al., Comp. Mol. Neurobiol., Pichon, Y., ed., Birkhäuser Verlag, Basel, Switzerland, pp. 172–209 (1993); Wafford, K. A., et al., J. Neurochem. 48:177–180 (1987)). These findings indicate that insect GABA receptors contain several drug binding sites with structural and target site specificities that are different from vertebrate receptor-binding sites (Hainzl, D., et al., Chem. Res. Toxicol. 11:1529–1535 (1998)). Selective insecticides, e.g. insecticides with favorable selective toxicity for insects relative to vertebrates, are based in part on this target-site specificity between the GABA receptors of insects and the $GABA_A$ receptors of vertebrates (Moffat, A. S., Science 261:550–551 (1993); Hainzl, D., et al., Chem. Res. Toxicol. 11:1529–1535 (1998)).

Radiolabeled ligand binding studies have considerably expanded our knowledge of insect GABA receptor pharmacology. Within the insect GABA receptor three distinct binding sites have been identified: the GABA receptor agonist binding site, a benzodiazepine binding site and a convulsant binding site (Lummis, S. C. R., Comp. Biochem. Physiol. 95C:1–8 (1990); Rauh, J. J., et al., TiPS 11:325–329 (1990)). The convulsant binding site of GABA receptors in pests is the major target site for many of the drugs and pesticides currently on the market.

Convulsant drugs and pesticides act at the GABA receptor in pest brain, ganglia and muscle as noncompetitive blockers. Inhibition of GABA receptors in pests produces neurotoxicity (e.g. convulsions, paralysis, coma and death). In the early 1980s, the pesticides lindane and cyclodienes (e.g.

dieldrin) were shown to antagonize the action of GABA in stimulating chloride uptake by various pest nerve and muscle preparations (Narahashi, T., *Pharmacol. Toxicol.* 78:1–14 (1996)). GABA receptors in pests are also blocked by picrotoxin, phenylpyrazole pesticides (e.g. Fipronil®), bicyclophosphorous esters (e.g. t-butylbicyclophosphoronthionate), and bicycloorthobenzoates (4-n-propyl-4'-ethynylbicycloorthobenzoate) (U.S. Pat. No. 5,853,002). These pesticides block transmission of signals by GABA, and are very effective on a wide range of economically important pests.

Unfortunately, many potent pesticides and their derivatives also act at the $GABA_A$ receptors of animals. For example, fipronil sulfone and desulfinyl fipronil, a metabolite and photoproduct of fipronil, respectively, are not only toxic to pests, but also to upland game birds, freshwater fish and invertebrates, and waterfowl. In addition, fipronil itself is a toxicant for mammals even without oxidation to the sulfone (Hainzl, D., et al., *Chem. Res. Toxicol.* 11:1529–1535 (1998)).

Pesticides that effectively kill pests but that have little toxicity for animals and humans remain the aim of current research efforts. The present invention addresses the need for the development and use of new and more efficacious pesticides that are highly toxic to pests but not to animals susceptible to pest infestation.

SUMMARY OF THE INVENTION

A first aspect of the present invention is directed to a method of inhibiting a pest GABA receptor, comprising contacting a pest GABA receptor with a compound of Formula I.

A second aspect of the invention is directed to a method for controlling pests, comprising contacting an animal, plant or object with a composition comprising a pesticidally effective amount of at least one compound of Formula I, or a salt thereof, and one or more pesticidally-acceptable diluents or carriers.

A third aspect of the invention is pesticidal compositions comprising at least one compound of Formula I, or a salt thereof, and one or more pesticidally-acceptable diluents or carriers.

A fourth aspect of the present invention is directed to novel compounds of Formula I.

A fifth aspect of the present invention is directed to a method for synthesizing compounds of Formula I.

A sixth aspect of the invention is directed to the use of one or more compounds of Formula I for the manufacture of collars or external devices, as well as to a treatment process relating thereto.

DETAILED DESCRIPTION OF THE PREFERRED EMBODIMENTS

A first aspect of the present invention is directed to a method of inhibiting a pest GABA receptor, comprising contacting one or more pest GABA receptors with one or more compounds of Formula I:

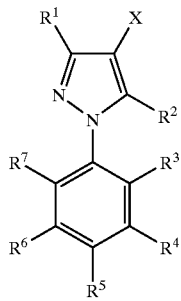

or a salt thereof, where
  $R^1$ represents $R^5O$, $R^5SO_2$, $R^5SO$ or $R^5S$ in which $R^5$ is optionally halogen substituted $C_{1-6}$ alkyl, optionally halogen substituted $C_{2-6}$ alkenyl, optionally halogen substituted $C_{2-6}$ alkynyl, $(C_{3-7}$ cycloalkyl)methyl; or benzyl, optionally substituted by halo, hydroxy, methoxy or ethoxy;
  X is halo, cyano, $C_{1-6}$ alkoxycarbonyl, $C_{2-6}$ alkynyl, optionally substituted $C_{6-14}$ aryl or an optionally substituted 5- to 7-membered heteroaromatic ring linked to thiazole via a carbon-carbon bond;
  $R^2$ is hydrogen, amino, chloro, bromo, iodo, cyano, $C_{1-6}$ alkoxy, $C_{1-6}$ alkyl or $C_{610}$ aryl; and
  $R^3$ –$R^7$ each represent hydrogen, halogen, straight- or branched-chain $C_{1-4}$ alkyl or $C_{1-4}$ alkoxy, either of which is unsubstituted or substituted by one or more halogen atoms, straight- or branched-chain $C_{1-4}$ alkylthio or $C_{1-4}$ alkylsulphinyl, either of which is substituted by one or more halogen atoms, nitro, cyano, or straight- or branched-chain $C_{1-4}$ alkylsulphonyl group which is unsubstituted or substituted by one or more halogen atoms.

A second aspect of the invention is directed to methods for controlling pests, comprising contacting an animal, plant or object with a composition comprising a pesticidally effective amount of at least one compound of Formula I, or a salt thereof, and one or more pesticidally-acceptable diluents or carriers. For purposes of the present invention, pests are undesired arthropods, in particular insects and arachnids, which are harmful to plants or animals susceptible to infestation by such arthropods. The methods of the present invention are suitable for combating animal pests, preferably arthropods, in particular insects and arachnids, encountered in and on companion animals, in agriculture, in forestry, in the protection of stored products and of materials, and in the hygiene field. Compounds employed in the methods of the invention have good plant tolerance or favorable safety to warm-blooded animals.

In particular, compounds of Formula I may be applied to control arthropods in compositions suitable for internal or external administration to vertebrates, or application for the control of arthropods in any indoor or outdoor area. Such compositions comprise at least one compound of Formula I and one or more diluents or carriers. The methods are more preferably used to reduce the viability and/or reproductive capacity of any ectoparasite. Preferred ectoparasites to target include arachnids, insects and leeches. More preferred ectoparasites include fleas and ticks. For example, the invention can be employed for killing fleas of the genus Ctenocephalides, in particular C. felis and C. canis, and ticks, in particular of the genus Rhipicephalus, especially R. sanguineus, as well as harvest ticks (Trombicula automnalis), Dermacentor variabilis, Dermacentor andersoni, Dermacentor occidentalis, Amblyomma americanum, Ixodes scapuris, and Ixodes pacificus.

A third aspect of the invention is directed to pesticidal compositions comprising a pesticidally effective amount of at least one compound of Formula I, or a salt thereof, and one or more pesticidally-acceptable diluents or carriers.

Preferred $R^1$ include $C_{1-4}$ alkylsulfonyl, $C_{1-4}$ alkylsulphinyl or $C_{1-4}$ alkylthio group, any of which is optionally halo-substituted. Useful values include —$SCH_3$, —$SOCH_3$, —$SO_2CH_3$, —$SCH_2CH_3$, —$SCH_2CH_2CH_3$, —$SCH_2CF_3$, cyclopropylmethylthio, 4-methoxybenzylthio, trifluoromethylthio and trifluoromethylsulfonyl. Most preferably, $R^1$ is —$SCH_3$. Preferred X include cyano, chloro, bromo, iodo, $C_{1-4}$ alkoxycarbonyl (such as ethoxycarbonyl and methoxycarbonyl), $C_{2-4}$ alkynyl (such as ethynyl and propynyl). Additional preferred X include the following optionally substituted aryl and heteroaryl groups: phenyl, naphthyl, pyridyl, thienyl, furanyl, isoxazolyl, thiazolyl, isothiazolyl, indolizinyl, isoindolyl, indolyl, indazolyl, quinolizinyl, quinolinyl, and isoquinolinyl. Preferred optional substituents on the Ar group include one or more of halogen, $C_{1-4}$ alkoxy, $C_{1-4}$ haloalkoxy, $C_{1-4}$ alkoxycarbonyl, nitro, amino, cyano, $C_{1-4}$ alkylthio, $C_{1-4}$ alkylsulfinyl or $C_{1-4}$ alkylsulfonyl.

Suitable values of X, when X is an optionally substituted aryl or heteroaryl group include 3-methyloxadiazin-5-yl, thiophen-2-yl; thiophen-3-yl, 5-methylthiophen-2-yl, 4-methylthiophen-2-yl, 5-chlorothiophen-2-yl, 4-chlorothiophen-2-yl, 5-methylcarbonylthiophen-2-yl, benzothiophen-2-yl, pyrimidin-6-yl, pyrazin-6-yl, phenyl, 2-methylphenyl, 2-fluorophenyl, 2-chlorophenyl, 2-trifluoromethylphenyl, 2-cyanophenyl, 2-methoxyphenyl, 2-methylthiophenyl, 2,4-dimethoxyphenyl, 3-methylphenyl, 3-isopropylphenyl, 3-methoxyphenyl, 2-fluorophenyl, 2-chlorophenyl, 2-trifluoromethylphenyl, 2-cyanophenyl, 2-methoxyphenyl, 2-methylthiophenyl, 3,5-di(trifluoromethyl)phenyl, 3-chloro-4-fluorophenyl, 3,4-dimethoxyphenyl, 3,4,5-trimethoxyphenyl, 1,3-benzodioxazol-5-yl, 4-methylphenyl, 4-fluorophenyl, 4-chlorophenyl, 4-bromophenyl, 4-trifluoromethylphenyl, 4-cyanophenyl, biphenyl, 4-isopropylphenyl, 4-methoxyphenyl, and 4-methylthiophenyl.

$R^2$ is preferably hydrogen, $NH_2$, chloro, bromo or cyano.

Preferred $R^3$ values are halogen, especially chloro. A preferred $R^4$ value is hydrogen. Preferred $R^5$ values are hydrogen, $C_{1-6}$ alkyl optionally substituted by one or more halogen atoms, $C_{1-6}$ alkoxy, optionally substituted by one or more halogen atoms. A preferred $R_6$ value is hydrogen and preferred $R^7$ value is halogen, especially chloro. More preferred combinations result in the following substitution patterns on the 1-phenyl ring: 2,4,6-trichloro-, 2-6-dichloro-4-difluoromethoxy-, 2-chloro-4-trifluoromethyl-, 2-bromo-6-4-trifluoromethyl-, 2,6-dibromo-4-trifluoromethyl- or 2-bromo-4-trifluoromethyl-, with 2,6-dichloro-4-trifluoromethyl and 2,6-dichloro-4-trifluoromethoxy being most preferred.

Examples of suitable compounds include:
1-[2,6-Dichloro-4-(trifluoromethyl)phenyl]-4-iodo-3-methylthiopyrazol-5-ylamine; 1-[2,6-Dichloro-4-(trifluoromethyl)phenyl]-4-chloro-3-methylthiopyrazol-5-ylamine;
1-[2,6-Dichloro-4-(trifluoromethyl)phenyl]-4-bromo-3-methylthiopyrazol-5-ylamine;
Methyl 5-amino-1-[2,6-dichloro-4-(trifluoromethyl) phenyl]-3-methylthiopyrazole-4-carboxylate;
5-Amino-1-[2,6-dichloro-4-(trifluoromethyl)phenyl]-3-methylthiopyrazole-4-carboxylic acid;
Ethyl 5-amino-1-[2,6-dichloro-4-(trifluoromethyl) phenyl]-3-methylthiopyrazole-4-carboxylate;
1-[2,6-Dichloro-4-(trifluoromethyl)phenyl]-4-(4-methylphenyl)-3-methylthiopyrazol-5-ylamine;
1-[2,6-Dichloro-4-(trifluoromethyl)phenyl]-4-phenyl-3-methylthiopyrazol-5-ylamine;
1-[2,6-Dichloro-4-(trifluoromethyl)phenyl]-4-phenyl-3-methylthiopyrazole;
1-[2,6-Dichloro-4-(trifluoromethyl)phenyl]-4-(2-methylphenyl)-3-methylthiopyrazol-5-ylamine;
1-[2,6-Dichloro-4-(trifluoromethyl)phenyl]-3-methylthio-4-[2-(trifluoromethyl)phenyl]pyrazol-5-ylamine;
1-[2,6-Dichloro-4-(trifluoromethyl)phenyl]-4-(2,4-dimethoxyphenyl)-3-methylthiopyrazol-5-ylamine;
1-[2,6-Dichloro-4-(trifluoromethyl)phenyl]-4-ethynyl-3-methylthiopyrazol-5-ylamine;
1-[2,6-Dichloro-4-(trifluoromethyl)phenyl]-4-(2-trimethylsilylethynyl)-3-methylthiopyrazol-5-ylamine;
1-[2,6-Dichloro-4-(trifluoromethyl)phenyl]-3-methylthio-4-pyrazin-2-ylpyrazol-5-ylamine;
1-[2,6-dichloro-4-(trfluoromethyl)phenyl]-3-methylthio-4-pyrazin-2-ylpyrazole;
1-[2,6-Dichloro-4-(trifluoromethyl)phenyl]-3-methylthio-4-(5-chlorothien-2-yl)pyrazol-5-ylamine;
1-[2,6-Dichloro-4-(trifluoromethyl)phenyl]-3-methylthio-4-(5-methoxycarbonylthien-2-yl)pyrazol-5-ylamine; and
1-[2,6-Dichloro-4-(trifluoromethyl)phenyl]-3-methylthio-4-(3-methyl-1,2,4-oxadiazin-5-yl)-2-ylpyrazol-5-ylamine.

Additional suitable compounds include:
5-Amino-1-[2,6-dichloro-4-(trifluoromethyl)phenyl]-3-methylthiopyrazole-4-carbonitrile;
1-[2,6-Dichloro-4-(trifluoromethyl)phenyl]-3-methylthiopyrazole4-carbonitrile;
5-Amino-1-[2,6-dichloro-4-(trifluoromethyl)phenyl]-3-ethylthiopyrazole-4-carbonitrile;
5-Amino-3-methylthio-1-[2,3,5,6-tetrafluoro-4-(trifluoromethyl)phenyl]pyrazole-4-carbonitrile;
5-Amino-3-methylthio-1-[4-(trifluoromethyl)phenyl] pyrazole-4-carbonitrile;
5-Amino-1-[2,6-dichloro-4-(trifluoromethyl)phenyl]-3-(methylsulfmyl)pyrazole-4-carbonitrile;
5-Amino-1-[2,6dichloro-4-(trifluoromethyl)phenyl]-3-(methylsulfonyl)pyrazole-4-carbonitrile;
1-[2,6-Dichloro-4-(trifluoromethyl)phenyl]-3-(methylsulfonyl)pyrazole-4-carbonitrile;
1-[2,6-Dichloro-4-(trifluoromethyl)phenyl]-3-(methylsulfinyl)pyrazole-4-carbonitrile; and
5-amino-1-[2,6-dichloro-4-(trifluoromethyl)phenyl]-3-[(4-methoxyphenyl)methylthio]pyrazole-4-carbonitrile.

A fourth aspect of the invention is directed to compounds within the generic scope of Formula I that are novel. Such compounds include compounds of Formula I or salts thereof, wherein $R^1$ represents $R^5O$, $R^5SO_2$, $R^5SO$ or $R^5S$ in which $R^5$ is optionally halogen substituted $C_{1-6}$ alkyl, optionally halogen substituted $C_{2-6}$ alkenyl, optionally halogen substituted $C_{2-6}$ alkynyl, $(C_{3-7}$ cycloalkyl)methyl; or benzyl, optionally substituted by halo, hydroxy, methoxy or ethoxy;

X is halo, $C_{1-6}$ alkoxycarbonyl, $C_{2-6}$ alkynyl, optionally substituted $C_{6-14}$ aryl or an optionally substituted 5- to 7-membered heteroaromatic ring linked to thiazole via a carbon-carbon bond;

$R^2$ is hydrogen, amino, chloro, bromo, iodo, cyano, $C_{1-6}$ alkoxy, $C_{1-6}$ alkyl or $C_{6-10}$ aryl; and $R^3$–$R^7$ each represent hydrogen, halogen, straight- or branched-chain $C_{1-4}$ alkyl or $C_{1-4}$ alkoxy, either of which is unsubstituted or substituted by one or more halogen atoms, straight- or branched-chain $C_{1-4}$ alkylthio or $C_{1-4}$ alkylsulphinyl, either of which is substituted by one or more halogen atoms, nitro, cyano, or straight- or branched-chain $C_{1-4}$ alkylsulphonyl group which is unsubstituted or substituted by one or more halogen atoms.

Preferred $R^1$ include $C_{1-4}$ alkylsulfonyl, $C_{1-4}$ alkylsulphinyl or $C_{1-4}$ alkylthio group, any of which is optionally halo-substituted. Useful values include —SCH$_3$, —SOCH$_3$, —SO$_2$CH$_3$, —SCH$_2$CH$_3$, —SCH$_2$CH$_2$CH$_3$, —SCH$_2$CF$_3$, cyclopropylmethylthio, 4-methoxybenzylthio, trifluoromethylthio and trifluoromethylsulfonyl. Most preferred $R^1$ is —SCH$_3$.

Preferred X include cyano, chloro, iodo, $C_{1-4}$ alkoxycarbonyl (such as ethoxycarbonyl and methoxycarbonyl), $C_{2-4}$ alkynyl (such as ethynyl and propynyl). Additional preferred X include the following optionally substituted aryl and heteroaryl groups: phenyl, naphthyl, pyridyl, thienyl, furanyl, isoxazolyl, thiazolyl, isothiazolyl, indolizinyl, isoindolyl, indolyl, indazolyl, quinolizinyl, quinolinyl, and isoquinolinyl. Preferred optional substituents on the Ar group include one or more of halogen, $C_{1-4}$ alkoxy, $C_{1-4}$ haloalkoxy, $C_{1-4}$ alkoxycarbonyl, nitro, amino, cyano, $C_{1-4}$ alkylthio, $C_{1-4}$ alkylsulfinyl or $C_{1-4}$ alkylsulfonyl.

Suitable values of X, when X is an optionally substituted aryl or heteroaryl group include 3-methyloxadiazin-5-yl, thiophen-2-yl; thiophen-3-yl, 5-methylthiophen-2-yl, 4-methylthiophen-2-yl, 5-chlorothiophen-2-yl, 4-chlorothiophen-2yl, 5-methylcarbonylthiophen2-yl, benzothiophen-2-yl, pyrimidin-6-yl, pyrazin-6-yl, phenyl, 2-methylphenyl, 2-fluorophenyl, 2-chlorophenyl, 2-trifluoromethylphenyl, 2-cyanophenyl, 2-methoxyphenyl, 2-methylthiophenyl, 2,4-dimethoxyphenyl, 3-methylphenyl, 3-isopropylphenyl, 3-methoxyphenyl, 2-fluorophenyl, 2-chlorophenyl, 2-trifluoromethylphenyl, 2-cyanophenyl, 2-methoxyphenyl, 2-methylthiophenyl, 3,5-di(trifluoromethyl)phenyl, 3-chloro-4-fluorophenyl, 3,4-dimethoxyphenyl, 3,4,5-trimethoxyphenyl, 1,3-benzodioxazol-5-yl, 4-methylphenyl, 4-fluorophenyl, 4-chlorophenyl, 4-bromophenyl, 4-trifluoromethylphenyl, 4-cyanophenyl, biphenyl, 4-isopropylphenyl, 4-methoxyphenyl, and 4-methylthiophenyl.

Preferred $R^2$ values hydrogen or NH$_2$.

Preferred $R^3$ values are halogen, especially chloro. A preferred $R^4$ value is hydrogen. Preferred $R^5$ values are hydrogen, $C_{1-6}$ alkyl optionally substituted by one or more halogen atoms, $C_{1-6}$ alkoxy, optionally substituted by one or more halogen atoms. A preferred $R_6$ value is hydrogen a and preferred $R^7$ value is halogen, especially chloro. More preferred combinations result in the following substitution patterns on the 1-phenyl ring: 2,4,6-trichloro-, 2-6-dichloro-4-difluoromethoxy-, 2-chloro-4-trifluoromethyl-, 2-bromo-6-4-trifluoromethyl-, 2,6-dibromo-4-trifluoromethyl- or 2-bromo-4-trifluoromethyl-, with 2,6-dichloro-4-trifluoromethyl and 2,6-dichloro-4-trifluoromethoxy being most preferred.

Examples of suitable compounds include:

1-[2,6-Dichloro-4-(trifluoromethyl)phenyl]-4-iodo-3-methylthiopyrazol-5-ylamine; 1-[2,6-Dichloro-4-(trifluoromethyl)phenyl]-4-chloro-3-methylthiopyrazol-5-ylamine;

1-[2,6-Dichloro-4-(trifluoromethyl)phenyl]-4-bromo-3-methylthiopyrazol-5-ylamine;

Methyl 5-amino-1-[2,6-dichloro-4-(trifluoromethyl)phenyl]-3-methylthiopyrazole-4-carboxylate;

5-Amino-1-[2,6-dichloro-4-(trifluoromethyl)phenyl]-3-methylthiopyrazole-4-carboxylic acid;

Ethyl 5-amino-1-[2,6-dichloro-4-(trifluoromethyl)phenyl]-3-methylthiopyrazole-4-carboxylate;

1-[2,6-Dichloro-4-(trifluoromethyl)phenyl]-4-(4-methylphenyl)-3-methylthiopyrazol-5-ylamine;

1-[2,6-Dichloro-4-(trifluoromethyl)phenyl]-4-pheny-3-methylthiopyrazol-5-ylamine;

1-[2,6-Dichloro-4-(trifluoromethyl)phenyl]-4-phenyl-3-methylthiopyrazole;

1-[2,6-Dichloro-4-(trifluoromethyl)phenyl]-4-(2-methylphenyl)-3-methylthiopyrazol-5-ylamine;

1-[2,6-Dichloro-4-(trifluoromethyl)phenyl]-3-methylthio-4-[2-(trifluoromethyl)phenyl]pyrazol-5-ylamine;

1-[2,6-Dichloro-4-(trifluoromethyl)phenyl]-4-(2,4-dimethoxyphenyl)-3-methylthiopyrazol-5-ylamine;

1-[2,6-Dichloro-4-(trifluoromethyl)phenyl]-4-ethynyl-3-methylthiopyrazol-5-ylamine;

1-[2,6-Dichloro-4-(trifluoromethyl)phenyl]-4-(2-trimethylsilylethynyl)-3-methylthiopyrazol-5-ylamine;

1-[2,6-Dichloro-4-(trifluoromethyl)phenyl]-3-methylthio-4-pyrazin-2-ylpyrazol-5-ylamine;

1-[2,6-dichloro-4-(trifluoromethyl)phenyl]-3-methylthio-4-pyrazin-2-ylpyrazole;

1-[2,6-Dichloro-4-(trifluoromethyl)phenyl]-3-methylthio-4-(5-chlorothien-2-yl)pyrazol-5-ylamine;

1-[2,6-Dichloro-4-(trifluoromethyl)phenyl]-3-methylthio-4-(5-methoxycarbonylthien-2-yl)pyrazol-5-ylamine; and 1-[2,6-Dichloro-4-(trifluoromethyl)phenyl]-3-methylthio-4-(3-methyl-1,2,4-oxadiazin-5-yl)-2-ylpyrazol-5-ylamine.

Definitions

The term "optionally substituted" when not otherwise explicitly provided for refers to the replacement of a hydrogen (or in the case of keto, two hydrogens) in a particular radical, with a functional group selected from the group consisting of halogen, trifluoromethyl, hydroxy, $C_{1-4}$ alkoxy, $C_{1-4}$ alkylthio, $C_{1-4}$ alkylsulfinyl, amino, nitro, cyano, $C_{2-6}$ carboxyalkyl, amidine, tetrazoly., mono- or di-($C_{1-6}$) alkylamino, mono- or di-($C_{6-10}$) arylamino, $C_{6-10}$ arlthio, $C_{6-10}$ arylsulfonyl, $C_{6-10}$ arylsulfinyl, oxide, $C_{6-10}$ aryl hydrazone, aminocarbonyl, mono- or di-($C_{1-6}$) alkylamino carbonyl and mono- or di-($C_{1-6}$) alkylamino-thiocarbonyl.

The term "alkyl" as employed herein by itself or as part of another group refers to both straight and branched chain radicals of up to 10 carbons, such as methyl, ethyl, propyl, isopropyl, butyl, t-butyl, isobutyl, pentyl, hexyl, isohexyl, heptyl, 4,4-dimethylpentyl, octyl, 2,2,4-trimethylpentyl, nonyl, and decyl. Preferably, the alkyl chain is 2 to 8 carbon atoms in length, more preferably from 2 to 4 carbon atoms in length.

The term "alkenyl" is used herein to mean a straight or branched chain radical of 2–10 carbon atoms, unless the chain length is limited thereto, including, but not limited to, ethenyl, 1-propenyl, 2-propenyl, 2-methyl-1-propenyl, 1-butenyl, 2-butenyl, and the like. Preferably, the alkenyl chain is 2 to 8 carbon atoms in length, more preferably, 2 to 4 carbon atoms in length.

The term "alkynyl" is used herein to mean a straight or branched chain radical of 2–10 carbon atoms, unless the chain length is limited thereto, wherein there is at least one triple bond between two of the carbon atoms in the chain, including, but not limited to, acetylene, 1-propylene, 2-propylene, and the like. Preferably, the alkynyl chain is 2 to 8 carbon atoms in length, more preferably from 2 to 4 carbon atoms in length.

In all instances herein where there is an alkenyl or alkynyl moiety as a substituent group, the unsaturated linkage, i.e., the vinylene or acetylene linkage is preferably not directly attached to a nitrogen, oxygen or sulfur moiety.

The term "aryl" as employed herein by itself or as part of another group refers to monocyclic or bicyclic aromatic groups containing from 6 to 14 carbons in the ring portion, preferably 6–10 carbons in the ring portion, such as phenyl, naphthyl, tetrahydronaphthyl, or biphenyl.

The term "heteroaryl" as employed herein refers to groups having 5 to 14 ring atoms; 6, 10 or 14 π electrons shared in a cyclic array; and containing carbon atoms and 1, 2 or 3 oxygen, nitrogen or sulfur heteroatoms (where examples of heteroaryl groups are: thienyl, benzo[b]thienyl, naphtho[2,3-b]thienyl, thianthrenyl, furyl, pyranyl, isobenzofuranyl, benzoxazolyl, chromenyl, xanthenyl, phenoxathiinyl, 2H-pyrrolyl, pyrrolyl, imidazolyl, pyrazolyl, pyridyl, pyrazinyl, pyrimidinyl, pyridazinyl, indolizinyl, isoindolyl, 3H-indolyl, indolyl, indazolyl, purinyl, 4H-quinolizinyl, isoquinolyl, quinolyl, phthalazinyl, naphthyridinyl, quinazolinyl, cinnolinyl, pteridinyl, 4αH-carbazolyl, carbazolyl, β-carbolinyl, phenanthridinyl, acridinyl, perimidinyl, phenanthrolinyl, phenazinyl, isothiazolyl, phenothiazinyl, isoxazolyl, furazanyl and phenoxazinyl groups).

The terms "alkoxy" refers to any of the above alkyl groups linked to an oxygen atom.

The term "halogen" or "halo" as employed herein by itself or as part of another group refers to chlorine, bromine, fluorine or iodine with chlorine being preferred.

The term "heteroatom" is used herein to mean an oxygen atom ("O"), a sulfur atom ("S") or a nitrogen atom ("N"). It will be recognized that when the heteroatom is nitrogen, it may form an $NR^yR^z$ moiety, wherein $R^y$ and $R^z$ are, independently from one another, hydrogen or C, to C, alkyl, or together with the nitrogen to which they are bound, form a saturated or unsaturated 5-, 6-, or 7-membered ring.

By the term "salts with pesticidally-acceptable bases" is meant salts the cations of which are known and accepted in the art for the formation of salts of pesticidally active acids for agricultural or horticultural use. When intended for application to vertebrates to combat infection or infestation by arthropods, the salts with bases used will be non-toxic. By the term "non-toxic" is meant salts with bases the cations of which are innocuous to the vertebrates at the doses administered and which do not vitiate the beneficial effects produced by the anion.

Preferably, the salts are water-soluble. Suitable salts with bases include alkali met al (e.g. sodium and potassium), alkaline earth met al (e.g. calcium and magnesium), ammonium and amine (e.g. diethanolamine, triethanolamine, octylamine, morpholine and dioctylmethylamine) salts. Where reference is made in the present specification to the compounds of Formula I such reference is intended to include also the salts with pesticidally-acceptable bases of compounds of Formula I where appropriate.

Compositions and Methods of Use

The compounds of Formula I can be employed as pesticides. For purposes of the present invention, pests are undesired arthropods, for example insects or arachnids, which are harmful to plants or animals susceptible to infestation by such arthropods.

Compounds of the invention are suitable for controlling animal pests, Preferably arthropods, inparticular insects and arachnids, encountered in and on companion animals, in agriculture, in forestry, in the protection of stored products and of materials, and in the hygiene field, and have good plant tolerance or favorable safety to warm-blooded animals.

Compounds of the invention while active against plant, hygiene and stored product pests, are particularly useful in the veterinary medicine sector, against animal ectoparasites such as scaly ticks, argasidae, scab mites, trombidae, flies (stinging and sucking), parasitic fly larvae, lice, hair lice, bird lice and fleas. For example, they have activity against fleas, such as fleas of the genus Ctenocephalides, in particular *C. felis* and *C. canis*, and ticks, such as ticks of the genus Rhipicephalus, especially *R. sanguineus*, as well as harvest ticks (*Trombicula automnalis*), *Dermacentor variabilis*, *Dermacentor andersoni*, *Dermacentor occidentalis*, *Amblyomma americanum*, *Ixodes scapularis*, and *Ixodes pacificus*. By virtue of their activity against fleas and ticks compounds of the invention are suitable for treating companion animals, such as dogs and cats.

Compounds of the invention are also suitable for the controlling of arthropods which infest useful animals in agriculture such as, for example, cattle, sheep, goats, horses, pigs, donkeys, camels, buffalo, rabbits, hens, turkeys, ducks, geese, bees, other domestic animals such as, for example, dogs, cats, cage birds, aquarium fish and so-called experimental animals such as, for example, hamsters, guinea pigs, rats and mice. The aim of combating these arthropods is to reduce fatalities and reductions in yield (in meat, milk, wool, skins, eggs, honey, etc.) so that the use of a compound according to the invention renders the keeping of animals more economic and more simple.

Compositions and methods of the present invention can be used to reduce the viability and/or reproductive capacity of any ectoparasite. Preferred ectoparasites to target include arachnids, insects and leeches. More preferred ectoparasites include fleas; ticks, including both hard ticks of the family Ixodidae (e.g., Ixodes and Amblyomma) and soft ticks of the family Argasidae (e.g., Ornithodoros, such as *O. parkeri* and *O. turicata*); flies, such as midges (e.g., Culicoides), mosquitos, sand flies, black flies, horse flies, horn flies, deer flies, tsetse flies, stable flies, myiasis-causing flies and biting gnats; ants; spiders; lice; mites; and true bugs, such as bed bugs and kissing bugs, including those carrying Chagas disease. Even more preferred ectoparasites include fleas, mosquitos, midges, sandflies, blackflies, ticks and kissing bugs, with fleas, ticks, mosquitos and midges being even more preferred.

Particularly preferred compositions and methods of the present invention targets fleas. Preferred fleas include Ctenocephalides, Xenopsylla, Pulex, Tunga, Nosopsyllus, Diamanus, Ctopsyllus and Echidnophaga fleas, with Ctenocephalides canis and Ctenocephalides felis fleas being even more preferred. For the purposes of illustration, many of the following embodiments discuss efficacy against fleas. Such discussion of efficacy against fleas is not intended, in any way, to limit the scope of the present invention.

A preferred aspect of the invention is directed towards killing fleas of the genus Ctenocephalides, in particular *C.*

*felis* and *C. canis*, and ticks, in particular of the genus Rhipicephalus, especially *R. sanguineus*, as well as harvest ticks (*Trombicula automnalis*), *Dermacentor variabilis, Dermacentor andersoni, Dermacentor occidentalis, Amblyomma americanum, Ixodes scapularis*, and *Ixodes pacificus*.

An aspect of the present invention is also the use of a compound of Formula I for the production of a collar or other external device intended to be attached to a pet, in particular cats and dogs.

This aspect of the invention is directed mainly towards fleas of the genus Ctenocephalides, in particular *C. felis* and *C. canis*, and ticks, in particular of the genus Rhipicephalus, especially *R. sanguineus*, as well as harvest ticks (*Trombicula automnalis*), *Dermacentor variabilis, Dermacentor andersoni, Dermacentor occidentalis, Amblyomma americanum, Ixodes scapularis*, and *Ixodes pacificus*.

Collars intended to eliminate common ectoparasites from cats and dogs consist of a matrix, usually a plastic matrix, which incorporates between 5 and 40% active substance and is capable of releasing it over time.

Slow release compositions that can be in the form of a collar or earrings for controlling harmful insects are also contemplated. Such formulations comprise from about 0.5 to about 25% active material, from about 75 to about 99.5% of a suitable resin, such as polyvinyl chloride and a catalytic amount of a plasticizer, such as dioctyl phthalate.

A subject of the present invention is thus a collar or other external device for a pet, in particular a cat or dog, made of a matrix in which is incorporated from 0.1 to 40% by weight, relative to the collar, of a substance which is active against ectoparasites such as fleas and ticks (anti-flea and anti-tick collar or other external device), this active substance being formed of at least one compound corresponding to Formula I.

One aspect of this method is non-therapeutic and in particular relates to the cleaning of animal hairs and skin by elimination of the parasites which are present, as well as their residues and secretions. The treated animals thus have hair which is more pleasant to look at and to feel.

The invention also relates to such a method for therapeutic purposes, intended to treat and prevent parasitoses having pathogenic consequences.

Compounds of Formula I may be applied to control arthropods in compositions suitable for internal or external administration to vertebrates or application for the control of arthropods in any indoor or outdoor area. Such compositions comprise at least one compound of Formula I and one or more diluents or excipients. Such compositions can be prepared in any manner known in the art.

Suitable means of applying compounds of Formula I include:

to persons or animals infested by or exposed to infestation by arthropods by parenteral, oral or topical application. Examples include incorporation of an active compound in feed or suitable orally-ingestible pharmaceutical formulations, edible baits, salt licks, dietary supplements, pour-on and spot-on formulations, sprays, baths, dips, showers,jets, dusts, greases, shampoos, creams, wax-smears and livestock self-treatment systems; to the environment in general or to specific locations where pests may lurk, including stored products, timber, household goods, and domestic and industrial premises, as sprays, fogs, dusts, smokes, wax-smears, lacquers, granules and baits, and in tricklefeeds to waterways, wells, reservoirs and other running or standing water; to domestic animals in feed to control fly larvae feeding in their feces;

to growing crops as foliar sprays, dusts, granules, fogs and foams; also as suspensions of finely divided and encapsulated compounds of Formula I;

as soil and root treatments by liquid drenches, dusts, granules, smokes and foams; and as seed dressings by liquid slurries and dusts.

Compositions suitable for administration to vertebrates include preparations suitable for oral, parenteral, percutaneous, e.g. pour-on, spot-on or other topical administration.

Compositions for oral administration comprise one or more of the compounds of Formula I in association with non-toxic veterinary carriers or coatings and include, for example, chewable treats, tablets, pills, capsules, pastes, gels, drenches, medicated feeds, medicated drinking water, medicated dietary supplements, slow-release boluses or other slow-release devices intended to be retained within the gastro-intestinal tract. Any of these may incorporate active ingredient contained within microcapsules or coated with acid-labile or alkali-labile or other pharmaceutically acceptable enteric coatings. Feed premixes and concentrates containing compounds of the present invention for use in preparation of medicated diets, drinking water or other materials for consumption by animals may also be used.

Compositions for parenteral administration include solutions, emulsions or suspensions in any suitable veterinary vehicle and solid or semisolid subcutaneous implants or pellets designed to release active ingredient over a protracted period and may be prepared and made sterile in any appropriate manner known to the art.

Compositions for percutaneous and topical administration include sprays, dusts, baths, dips, showers, jets, greases, shampoos, creams, wax-smears, or spot-on or pour-on preparations. Compounds of Formula I can also be administered with the aid of shaped articles which contain active compound, such as neck bands, ear tags, tail tags, limb bands, halters, marking devices and the like devices (e.g. ear tags) attached externally to animals in such a way as to provide local or systemic arthropod control.

Solid or liquid baits suitable for controlling arthropods comprise one or more compounds of Formula I and a carrier or diluent which may include a food substance or some other substance to induce consumption by the arthropod.

Medicated feeds which comprise a compound of Formula I and arthropodicidally- acceptable salts thereof and an edible carrier or diluent form an additional feature of the present invention.

Liquid compositions include water miscible concentrates, emulsifiable concentrates, flowable suspensions, wettable or soluble powders containing one or more compounds of Formula I which may be used to treat substrates or sites infested or liable to infestation by arthropods including premises, outdoor or indoor storage or processing areas, containers or equipment and standing or running water.

Solid homogenous or heterogenous compositions containing one or more compounds of Formula I, for example granules, pellets, briquettes or capsules, may be used to treat standing or running water over a period of time. A similar effect may be achieved using trickle or intermittent feeds of water dispersible concentrates.

Compositions in the form of aerosols and aqueous or non-aqueous solutions or dispersions suitable for spraying, fogging and low- or ultra-low volume spraying may also be used.

The compositions of the invention, besides at least one compound of Formula I and, if appropriate, besides extenders and auxiliaries, may also comprise at least one surfactant (wetting, dispersing and emulsifying agents).

The wetting, dispersing and emulsifying agents which may be present, particularly in wettable powders, may be of the ionic or non-ionic types, for example sulphoricinoleates, quaternary ammonium derivatives or products based upon condensates of ethylene oxide with nonyl- and octylphenol, or carboxylic acid esters of anhydrosorbitols which have been rendered soluble by etherification of the free hydroxy groups by condensation with ethylene oxide, or mixtures of these types of agents. Wettable powders may be treated with water immediately before use to give suspensions ready for application.

Liquid compositions for the application of the compounds of Formula I may take the form of solutions, suspensions and emulsions of the compounds of Formula I optionally encapsulated in natural or synthetic polymers, and may, if desired, incorporate wetting, dispersing or emulsifying agents. These emulsions, suspensions and solutions may be prepared using aqueous, organic or aqueous-organic diluents, for example acetophenone, isophorone, toluene, xylene, mineral, animal or vegetable oils, and water soluble polymers (and mixtures of these diluents), which may contain wetting, dispersing or emulsifying agents of the ionic or non-ionic types or mixtures thereof, for example those of the types described above. When desired, the emulsions containing the compounds of Formula I may be used in the form of self-emulsifying concentrates containing the active substance dissolved in the emulsifying agents or in solvents containing emulsifying agents compatible with the active substance, the simple addition of water to such concentrates producing compositions ready for use.

Compositions containing compounds of Formula I which may be applied to control arthropod pests, may also contain synergists (e.g. piperonyl butoxide or sesamex), stabilizing substances, other insecticides, acaricides, plant nematocides, anthelmintics or anticoccidials, fungicides (agricultural or veterinary as appropriate e.g. benomyl, iprodione), bactericides, arthropod or vertebrate attractants or repellents or pheromones, reodorants, flavouring agents, dyes and auxiliary therapeutic agents, e.g. trace elements. These may be designed to improve potency, persistence, safety, uptake where desired, spectrum of pests controlled or to enable the composition to perform other useful functions in the same animal or area treated.

Examples of other pesticidally-active compounds which may be included in, or used in conjunction with, the compositions of the present invention are: chlorpyrifos, demeton-S-methyl, disulfoton, ethoprofos, fenitrothion, malathion, parathion, triazophos, amitraz, cypermethrin, deltamethrin, fenpropathrin, fenvalerate, permethrin, aldicarb, carbosulfan, pirimicarb, bendiocarb, teflubenzuron, dicofol, endosulfan, lindane, benzoximate, avermectins, ivermectin, milbemycins, thiophanate, trichlorfon, dichlorvos, diaveridine and dimetridazole.

A "pesticidally effective amount" refers to an amount of compound that will be toxic to one or more pests under the conditions administered. When administered to vertebrates parenterally, orally or by percutaneous or other means, the dosage of compounds of Formula I will depend upon the species, age and health of the vertebrate and upon the nature and degree of its actual or potential infestation by arthropod pest. Determination of optimal ranges of effective amounts of each component in a composition is within the skill of the art. A single dose of 0.1 to 100 mg, preferably 2.0 to 20.0 mg, per kg body weight of the animal per month or doses of 0.01 to 20.0 mg, preferably 0.1 to 5.0 mg, per kg body weight of the animal per day for sustained medication are generally suitable by oral, topical or parenteral administration. By use of If sustained release formulations or devices, the daily doses required over a period of months may be combined and administered to animals on a single occasion.

Compounds are screened for GABA receptor inhibiting activity using in vitro assays that measure the ability of a test compound to bind to pest and/or mammal GABA receptors. These assays, exemplified herein in working Examples 15 and 16, employ membranes possessing active GABA receptors. Preferred compounds have selectivity towards arthropod GABA receptor versus mammalian GABA receptor. Imediately following is a description of methods for forming such membranes. Ectoparacitidal activity can be determined in vivo. Suitable tests are described in working Examples 17 and 18.

Preparation of Housefly Membranes Possessing Active GABA Receptors

Newly emerged houseflies (*Musca domestica*, available from Rincon-Vitova Insectaries, Inc., Ventura, Calif.) were sedated with carbon dioxide gas, collected in 50 mL polypropylene conical tubes, and immediately frozen by submersion in liquid nitrogen. Unless specified, all of the following work was performed at 0–4° C. After removal from liquid nitrogen, the tubes of frozen houseflies were shaken vigorously by hand to decapitate the houseflies. The decapitated houseflies were then passed through a #10 mesh tissue sieve to separate the heads, which went through the sieve, from the larger abdomen, thoraxes, and residual intact houseflies that did not pass through the sieve. Contaminating wings were removed by holding a vacuum nozzle approximately 4 cm above the heads, and contaminating legs were separated from the heads by passage through a #15 mesh screen. All remaining debris were removed from the pool of heads using forceps. The purified heads were collected in 50 mL polypropylene conical tubes and stored in liquid nitrogen until processed further.

About 13 g of purified housefly heads were suspended in about 65 mL of 10% sucrose buffer (10% sucrose (w/w) in 10 mM Tris, pH 7.5). The heads were homogenized for about 1 minute, using a Tissumizer™ homogenizer equipped with a SDT-100EN probe (available from Tekmar-Dohrmann, Cincinnati, Ohio) running at 70% of its maximum speed. The extract was further homogenized by about 5 passes through a 40 mL Dounce tissue grinder. The extract was then centrifuged at about 500×g for about 5 minutes to pellet large debris. The supernatant was collected; the pellet was washed with an additional 65 mL of 10% sucrose buffer and centrifuged at 500×g for about 5 minutes. The second supernatant was collected and combined with the first supernatant, and the pool was filtered through a 100$\mu$ CellMicroSieve™ mesh to remove residual debris (available from BioDesign of New York, Carmel, N.Y.).

Neuronal membranes containing active GABA receptors were collected via sucrose density centrifugation by the following method. About 8 mL of 35% sucrose buffer (35% sucrose (w/w) in 10 mM Tris, pH 7.5), were dispensed into each of six 38 mL ultracentrifuge tubes. These layers were overlaid with about 8 mL of 20% sucrose buffer (20% sucrose (w/w) in 10 mM Tris, pH 7.5), and finally overlaid with about 20 mL of filtered extract supernatant. The tubes were centrifuged at about 120,000×g for about 100 min at 4° C. After centrifugation, the 10% sucrose layer and most of the 20% sucrose layer were removed by aspiration. The membranes at the interface of the 20% sucrose and 35% sucrose layers were collected, pooled, diluted with 10% sucrose buffer, and centrifuged at about 120,000×g for about 40 min at 4° C. After centrifugation, the supernatant was discarded, and the pellets resuspended in about 6.5 mL of assay buffer (10 mM phosphate, 300 mM NaCl, pH 7.5) using a 10 mL Potter-Elvehjem tissue grinder with a Teflone pestle. Protein concentration was determined by the Bio-Rad Protein Assay (available from Bio-Rad Laboratories, Hercules, Calif.) using bovine serum albumin as a standard. The membranes were aliquoted and stored in liquid nitrogen for up to 2 months before use.

Preparation of Mouse Brain Membranes Possessing Active GABA Receptors

Mouse brains were obtained from carbon dioxide-asphyxiated Swiss-Webster mice, washed with phosphate-buffered saline, and used either fresh or after storage at −80° C. for up to 10 months. Unless specified, all preparation steps were performed at 0–4° C. For each preparation, 20 brains were suspended in about 40 mL of 0.32 M sucrose and homogenized for about 2 minutes, using a Tissumizer™ homogenizer equipped with a SDT-100EN probe (available from Tekmar-Dohrmann, Cincinnati, Ohio) running at 50% of its maximum speed. The extract was centrifuged for about 5 min at about 1000×g to pellet intact brain tissue. The supernatant was retained and the pellet washed with an additional 40 mL of 0.32 M sucrose and centrifuged at 1000×g for about 5 minutes. The 1000×g supernatants were combined and centrifuged at about 10,000×g for about 20 min to pellet membranes. The 10,000×g supernatant was discarded and the pellet was resuspended in about 20 mL of water containing 1 mM EDTA. The sample was dialyzed two times for about 3 hours each against about 3 L of water. The sample was then centrifuged at about 25,000×g for about 30 min to pellet the membranes. After centrifugation, the supernatant was discarded and the pellet recovered. The protein concentration of the pellet was determined by the Bio-Rad Protein Assay (available from Bio-Rad Laboratories, Hercules, Calif.) using bovine serum albumin as a standard. The membranes were aliquoted and stored at −80° C. for up to 6 months before use.

Preparation of Compounds

The present invention is also directed to the multi-step synthesis of compounds of Formula I, including intermediates and intermediate reaction steps as herein described.

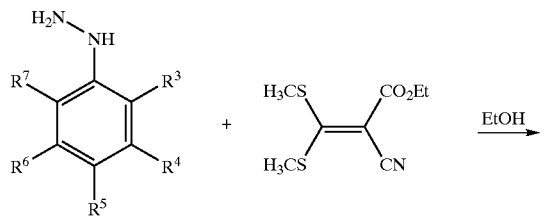

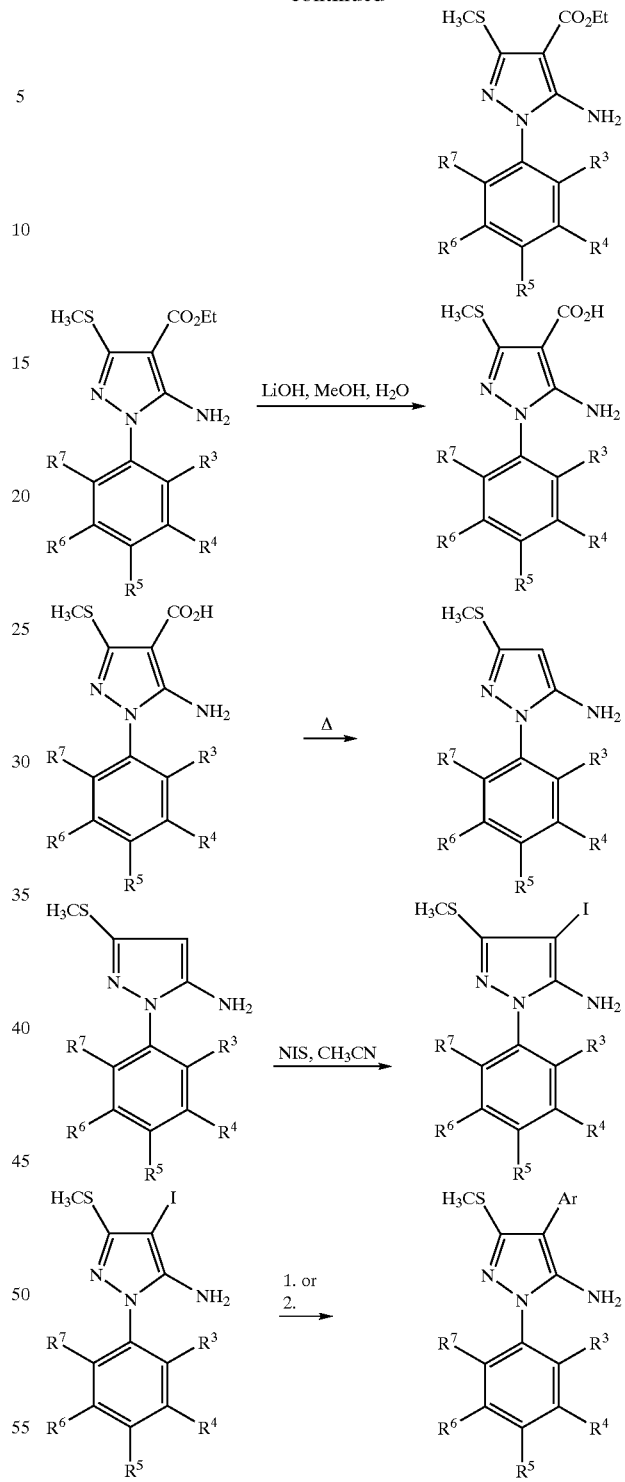

where 1 is treatment with an aryl boronic acid (ArB(OH)$_2$), and tetrakis (triphenylphosphine) palladium; and 2 is treatment with an aryltributyl tin compound and tetrakis (triphenylphosphine) palladium.

Compounds of the present invention can be synthesized according to methods outlined in the schemes appearing below.

Scheme 1
Synthesis of 1-Aryl-4-Substitued Pyrazoles

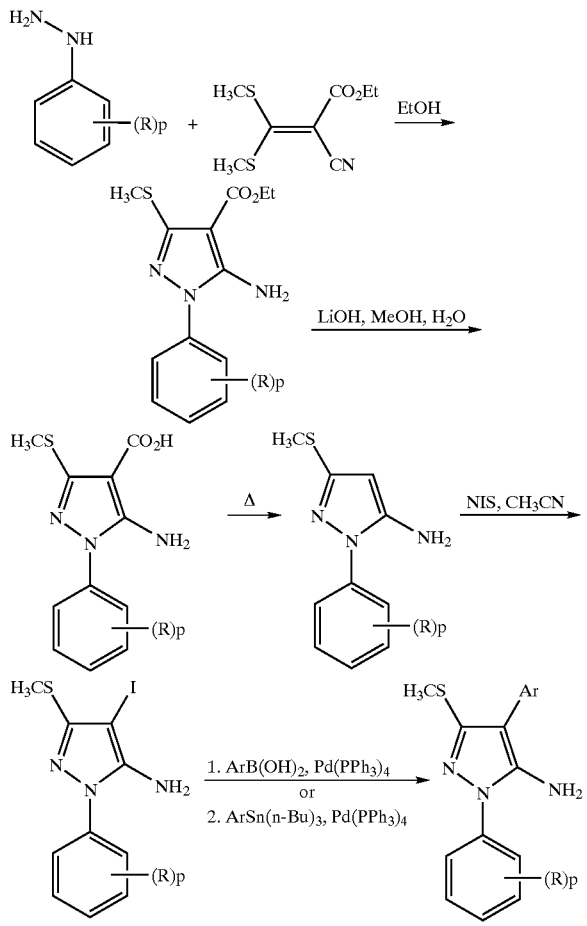

where R has the same values as defined for $R^3$–$R^7$ above, and p is 1–5, preferably 1–3.

The included examples are illustrative, but not limiting, of the compounds, methods and compositions of the present invention. Other suitable modifications and adaptations of the variety of conditions and parameters normally encountered and obvious to those skilled in the art are within the spirit and scope of the invention.

Examples 1 through 5 illustrate steps 1 through 5, respectively, of the synthesis method depicted by Scheme 1, above.

EXAMPLE 1

Ethyl 5-Amino-1-[2,6-dichloro-4-(tifluoromethyl) phenyl]-3-methylthiopyrazole-4-carboxylate (21); and Methyl 5-Amino-1-[2,6-dichloro-4-(trifluoromethyl)phenyl]-3-methylthiopyrazole-4-carboxylate (26)

A solution of 2,6-dichloro-4-trifluoromethylphenyl hydrazine (245 mg, 1.0 mmol) and 3,3-(bismethylthio)-2-cyanoacrylic acid ethyl ester (217 mg, 1.0 mmol) in isopropyl alcohol (15 mL) was heated at reflux for 16 h. The solvent was removed under reduced pressure and the desired product obtained after chromatographic separation (silica gel) using ethyl acetate-hexanes (1:9) affording 310 mg (yield: 75%) of compound 21 as a white solid. $^1$H-NMR ($\delta$, CDCl$_3$): 1.40 (3H, t, J=7.2 Hz); 2.48 (s, 3H); 7.76 (2H, s). MS: M+1=414 (calculated: 414).

By proceeding in a similar manner, but replacing the ethyl ester with the methyl ester, methyl 5-amnino-1-[2,6-dichloro-4-(trifluoromethyl)phenyl]-3-methylthiopyrazole-4-carboxylate (26) was prepared. $^1$H-NMR ($\delta$, CDCl$_3$): 7.76 (s, 2H); 5.1 (2H, broad); 3.88 (3H, s); 2.49 (s, 3H). MS: M+1=400 (calculated: 400).

EXAMPLE 2

5-Amino-1-[2,6-dichloro-4(trifluoromethyl)phenyl]-3-methylthiopyrazole-4-carboxylic Acid (27)

Ethyl ester 21 (207 mg, 0.5 mmol) was dissolved in a solution of LiOH (96 mg, 4 mmol) in methanol water (7 mL, 9:1). The resulting solution was stirred at reflux for 16 h, and then cooled down to room temperature. Methanol was removed at reduced pressure and the aqueous suspension was taken to pH 4 by addition of acetic acid and extracted with methylene chloride (3×30 mL). The organic fractions were combined, dried (MgSO$_4$), and the solvent evaporated under reduced pressure to give 173 mg (90%) of pure acid 27 $^1$H-NMR ($\delta$, CDCl$_3$): 2.5 (s, 3H); 7.77 (2H, s). MS: M+1=387 (calculated: 387).

EXAMPLE 3

1-[2,6-Dichloro-4-(tinfluoromethyl)phenyl]-3-methylthiopyrazol-5-ylamine (2)

The carboxylic acid 27 (1.16 g, 30 mmol) was heated at 200° C. for 20 min. After cooling down to room temperature, the reaction product was purified by flash chromatography (ethyl acetate:hexanes 15:85) to yield compound 2 (665 mg, 65%). $^1$H-NMR ($\delta$, CDCl$_3$): 2.5 (s, 311); 7.75 (2H, s); 5.67 (1H, s). MS: M+1=343 (calculated: 343).

EXAMPLE 4

1-[2,6-Dichloro-4-(trifluoromethyl)phenyl]-4-halo-3-methylthiopyrazol-5-ylamine (4-Iodo, 20), (4-Chloro, 18) and (4-Bromo, 19)

A solution of compound 4 (340 mg, 1.0 mmol) in acetonitrile (5 mL) was treated at 0° C. with N-iodosuccinimiide (1.2 eq, 270 mg, 1.2 mmol). The solution was stirred at room temperature for 30 min and t hen concentrated in vacuum. The residue was taken with methylene chloride and washed with water and Na$_2$S$_2$O$_3$ (10% aqueous solution). The organic phase was dried (MgSO$_4$), the solvents removed under reduced pressure, and the desired product (1-[2,6-dichloro4-(trifluoromethyl)phenyl]-4-iodo-3-methylthiopyrazol-5-ylane, 20) obtained by separation through flash chromatography (ethyl acetate:hexanes 15:85). $^1$H-NMR ($\delta$, CDCl$_3$): 2.54 (s, 3H); 7.65 (2H, s). MS: M+1=469 (calculated: 469).

In a simiar manner, but using N-chlorosuccinimeide, 1-[2,6-dichloro-4-(trifluoromethyl)phenyl]-4- chloro-3-methylthiopyrazol-5-ylamine (18) was made. $^1$H-NMR ($\delta$, CDCl$_3$): 2.53 (s, 3H); 7.74 (2H, s). MS: M+1=386 (calculated: 376).

In a similar manner, but using N-bromosuccinimide, 1-[2,6-dichloro-4-(trifluoromethyl)phenyl]-4-bromo-3-methylthiopyrazol-5-ylamine (19) was made $^1$H-NMR ($\delta$, CDCl$_3$): 2.54 (s, 3H); 7.65 (2H, s). MS: M+1=421 (calculated: 421).

EXAMPLE 5

5-Aminol4-substituted Pyrazoles (30, 32–41, 45, 47, 49–76, 78, and 79)

General Procedure Using Boronic Acids

A solution of 4-iodopyrazole 20 (47 mg, 0.1 mmol) and the corresponding boronic acid (2 eq, 0.2 mmol) in toluene (5 mL) was placed in a vial. NaHCO$_3$ (sat soln, 2 mL), ethanol (2 mL), and tetrakis(triphenylphosphine)palladium (0) (12 mg, 0.10 eq, 0.01 mmol) was added. The mixture was he ate d at 100° C. for 6 h. After cooling down the aqueous layer was separated, and the organic solvents were removed at reduced pressure. The desired product was obtained by flash chromatography (EtOAc-hexanes).

Following this general procedure were obtained:

1-[2,6-Dichloro-4-(trifluoromethyl)phenyl]-4-(2-methylphenyl)-3-methylthiopyrazol-5-ylamine (47): $^1$H-NMR ($\delta$, CDCl$_3$): 2.29 (3H, s); 2.49 (3H, s); 3.38 (2H, broad); 7.3 (4H, m); 7.75 (2H, s). MS: M+1=433 (calculated: 433).

1-[2,6-Dichloro-4-(trifluoromethyl)phenyl]-3-methylthio-4-[2-(trifluoromethyl)phenyl]pyrazol-5-ylamine (51): $^1$H-NMR ($\delta$, CDCl$_3$): 2.4 (3H, s); 7.3–7.6 (3H, m); 7.75–7.9 (3H, m). MS: M+1=486 (calculated: 486).

1-[2,6-Dichloro-4-(trifluoromethyl)phenyl]-4-(2,4-dimethoxyphenyl)-3-methylthiopyrazol-5-ylamine (55): $^1$H-NMR ($\delta$, CDCl$_3$): 2.48 (3H, s); 3.83 (3H, s); 3.85 (3H, s); 6.56 (1H, $\delta$, J=2.41); 6.62 (1H, dd, J=8.3; 2.4); 7.41 (1H, d, J=8.4 Hz); 7.74 (2H, s). MS: M+1= 479 (calculated: 479).

General Procedure Using Organotin Compounds

A solution of 4-iodopyrazole 20 (47 mg, 0.1 mmol) and the corresponding aryltributyltin compound (2 eq, 0.2 mmol) in N,N-DMF (5 mL) containing tetrakis (triphenylphosphine) palladium (0) (12 mg, 0.1 eq, 0.01 mmol) was heated at 75° C. for 12 h. After cooling, the reaction mixture was poured into water, and extracted with ethyl acetate (3×30 mL). The organic fractions were combined and concentrated under reduced pressure. The desired product was obtained by flash chromatography (EtOAc-hexanes).

Following this general procedure were obtained:

1-[2,6-Dichloro-4-(trifluoromethyl)phenyl]-4-(2-trimethylsilylethynyl)-3-methylthiopyrazol-5-ylamine (28): $^1$H-NMR ($\delta$, CDCl$_3$): 0.25 (9H, s); 2.51 (3H, s); 4.12 (2H, broad); 7.73 (2H, s). MS: M+1=439 (calculated: 439);

1-[2,6-Dichloro-4-(trifluoromethyl)phenyl]-3-methylthio-4-pyrazin-2-ylpyrazol-5-ylamine (41): $^1$H-NMR ($\delta$, CDCl$_3$): 2.63 (3H, s); 5.76 (2H, broad); 7.78 (2H, s); 8.28 (1H, d, J=2.6 Hz); 8.42 (1H, dd, J=1.5; 2.4 Hz); 9.2 (1H, d, J=1.5 Hz). MS: M+1=420 (calculated: 420).

Scheme 2 illustrates a generalized synthetic method for forming compounds of the invention having a 4-cyano substitution.

Scheme 2
Preparation of 1-Aryl-4-Cyanopyrazoles

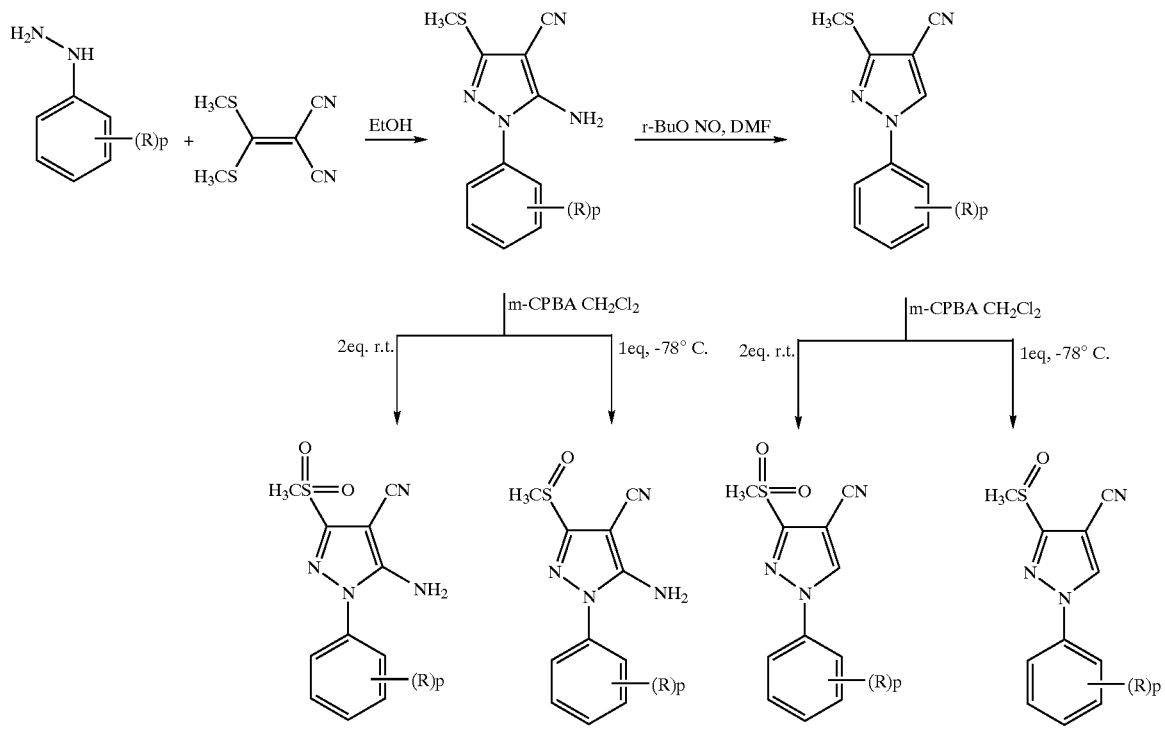

EXAMPLE 6

4-Cyanopyrazoles (80–100)

A solution of the corresponding substituted phenylhydrazine (1.0 mmol) and 3,3-(bismethylthio)-2-cyanoacrylonitrile (170 mg, 1.0 mmol) in isopropyl alcohol (15 mL) was heated at reflux for 16 h. The solvent was removed under reduced pressure and the desired product obtained after chromatographic separation (silica gel) using ethyl acetate:hexanes (Y=50–90%).

Following this general procedure were obtained:

5-Amino-1-[2,6-dichloro-4-(trifluoromethyl)phenyl]-3-methylthiopyrazole-4-carbonitrile (5): $^1$H-NMR ($\delta$, CDCl$_3$): 2.6 (3H, s); 7.9 (2H, s). MS: M+1=367 (calculated: 367);

5-Amino-3-methylthio-1-[2,3,5,6-tetrafluoro-4-(trifluoromethyl)phenyl]pyrazole-4-carbonitrile (83): $^1$H-NMR ($\delta$, CDCl$_3$): 4.6 (2H; s, broad); 2.55 (3H; s). MS: M+1=371 (calculated: 371);

5-Amino-3-methylthio-1-[4-(trifluoromethyl)phenyl]pyrazole-4-carbonitrile (92): $^1$H-NMR ($\delta$, CDCl$_3$): 7.81 (2H, d, J=8.5 Hz); 7.68 (2H, d, J=8.5 Hz); 4.6 (2H, broad); 2.6 (3H, s). MS: M+1=299 (calculated: 299).

EXAMPLE 7

5-Amino-1-[2,6-dichloro-4-(ttifluoromethyl)phenyl]-3-(methylsulfinyl)pyrazole-4-carbonitrile (6)

A solution of methylsulfide 5 (37 mg, 0.1 mmol) in dichloromethane (5 mL) was cooled down to −78° C. 3-Chloroperoxybenzoic acid (55%, 0.1 mmol, 32 mg) was added, and the reaction mixture stirred at low temperature for 1 h. The reaction was quenched by addition of sodium thiosulfate (5% in water), and diluted with dichloromethane. The organic phase was washed with sodium bicarbonate (5% in water) and brine. The organic layer was dried with magnesium sulfate, and the solvent removed under reduced pressure. The crude solid thus obtained was purified by flash chromatography, eluting with ethyl acetate-hexanes, to produce compound 6, (24 mg, 63%). $^1$H-NMR ($\delta$, CDCl$_3$/CD$_3$OD): 7.9 (2H, s); 4.2 (3H, s); 3.0 (3H; s). MS: M+1=383 (calculated: 383).

EXAMPLE 8

5-Amino-1-[2,6-dichloro-4-(tyifluoromethyl)phenyl]-3-(methylsulfonyl)pyrazole-4-carbonitile (7)

A solution of methylsulfide 5 (37 mg, 0.1 mmol) in dichloromethane (5 mL) was treated at room temperature with 3-chloroperoxybenzoic acid (55%, 0.2 mmol, 64 mg), and the reaction mixture stirred at room temperature for 1 h. The reaction was quenched by addition of sodium thiosulfate (5% in water), and diluted with dichloromethane. The organic phase was washed with sodium bicarbonate (5% in water) and brine. The organic layer was dried with magnesium sulfate, and the solvent removed under reduced pressure. The crude solid thus obtained was purified by flash chromatography, eluting with ethyl acetate-hexanes, to produce compound 7 (30 mg, 75%). $^1$H-NMR ($\delta$, CDCl$_3$): 3.27 (3H, s); 4.9 (2H, broad); 8.05 (2H; s). MS: M+1=399 (calculated: 399).

EXAMPLE 9

1-[2,6-Dichloro-4-(trifluoromethyl)phenyl]-3-methylthiopyrazole-4-carbonitrile (8)

A solution of methylsulfide 5 (37 mg, 0.1 mmol) in DMF (5 mL) was warmed up to 65° C. and treated dropwise with excess isoamyl nitrite. After a few minutes nitrogen gas bubbled off the reaction mixture. The stirring was continued for 30 min. The reaction was cooled down to room temperature, diluted with ethyl ether (10 mL) and washed with brine (5×15 mL). The organic layer was dried (magnesium sulfate) and the solvents removed at reduced pressure, leaving a dark oil residue The desired product was obtained upon flash chromatography eluting with ethyl acetate-hexanes (5%), to yield 19 mg (54%) of desired product 8. $^1$H-NMR ($\delta$, CDCl$_3$): 7.95 (1H, s); 7.78 (2H, s); 2.6 (3H; s). MS: M+1=352 (calculated: 352).

EXAMPLE 10

1-[2,6-Dichloro-4-(trifluoromethyl)phenyl]-3-(methylsulfonyl)pyrazole-4-carbonittile (10)

A solution of methylsulfide 8 (35 mg, 0.1 mmol) in dichloromethane (5 mL) was treated at room temperature with 3-chloroperoxybenzoic acid (55%, 0.2 mmol, 64 mg), and the reaction mixture stirred at room temperature for 1 h. The reaction was quenched by addition of sodium thiosulfate (5% in water), and diluted with dichloromethane. The organic phase was washed with sodium bicarbonate (5% in water) and brine. The organic layer was dried with magnesium sulfate, and the solvent removed under reduced pressure. The crude solid thus obtained was purified by flash chromatography, eluting with ethyl acetate-hexanes, to produce compound 10 (25 mg, 65%). MS: M+1=384 (calculated: 384).

EXAMPLE 11

1-[2,6-Dichloro-4-(tyifluoromethyl)phenyl]-3-(methylsulfinyl)pyrazole-4-carbonitrile (9)

A solution of methylsulfide 8 (35 mg, 0.1 mmol) in dichloromethane (5 mL) was cooled down to −78° C. 3-Chloroperoxybenzoic acid (55%, 0.1 mmol, 32 mg) was added, and the reaction mixture stirred at low temperature for 1 h. The reaction was quenched by addition of sodium thiosulfate (5% in water), and diluted with dichloromethane. The organic phase was washed with sodium bicarbonate (5% in water) and brine. The organic layer was dried with magnesium sulfate, and the solvent removed under reduced pressure. The crude solid thus obtained was purified by flash chromatography, eluting with ethyl acetate-hexanes (40%), to produce compound 8, (25 mg, 63%). MS: M+1=400 (calculated: 400).

EXAMPLE 12

1-[2,6-dichloro-4-(trifluoromethyl)phenyl]-3-methylthio-4-pyrazin-2-ylpyrazole (42)

A solution of aminopyrazole 41 (42 mg, 0.1 mmol) in DMF (5 mL) was warmed up to 65° C. and treated dropwise with excess isoamyl nitrite (150 mL). Stirring was continued for 30 min. The reaction was cooled down to room temperature, diluted with ethyl ether (10 mL) and washed with brine (5×15 mL). The organic layer was dried (magnesium sulfate) and the solvents removed at reduced pressure, leaving a dark oil residue. The desired product was obtained upon flash chromatography eluting with ethyl acetate-hexanes (5–10%), to yield 14 mg (35%) of desired product. $^1$H-NMR ($\delta$, CDCl$_3$): 2.63 (3H, s); 7.78 (2H, s); 8.1 (1H, s); 8.28 (1H, d, J=2.5 Hz); 8.4 (1H, dd, J=1.4; 8.4 Hz); 9.2 (1H, d, J=1.5 Hz). MS: M+1=404 (calculated: 404).

Scheme 3 depicts a generalized scheme for forming compounds having various alkylthio groups at the 3-position.

Scheme 3
Synthesis of 1-Aryl-S-Alkyl-4-Cyano-5-Aminopyrazoles

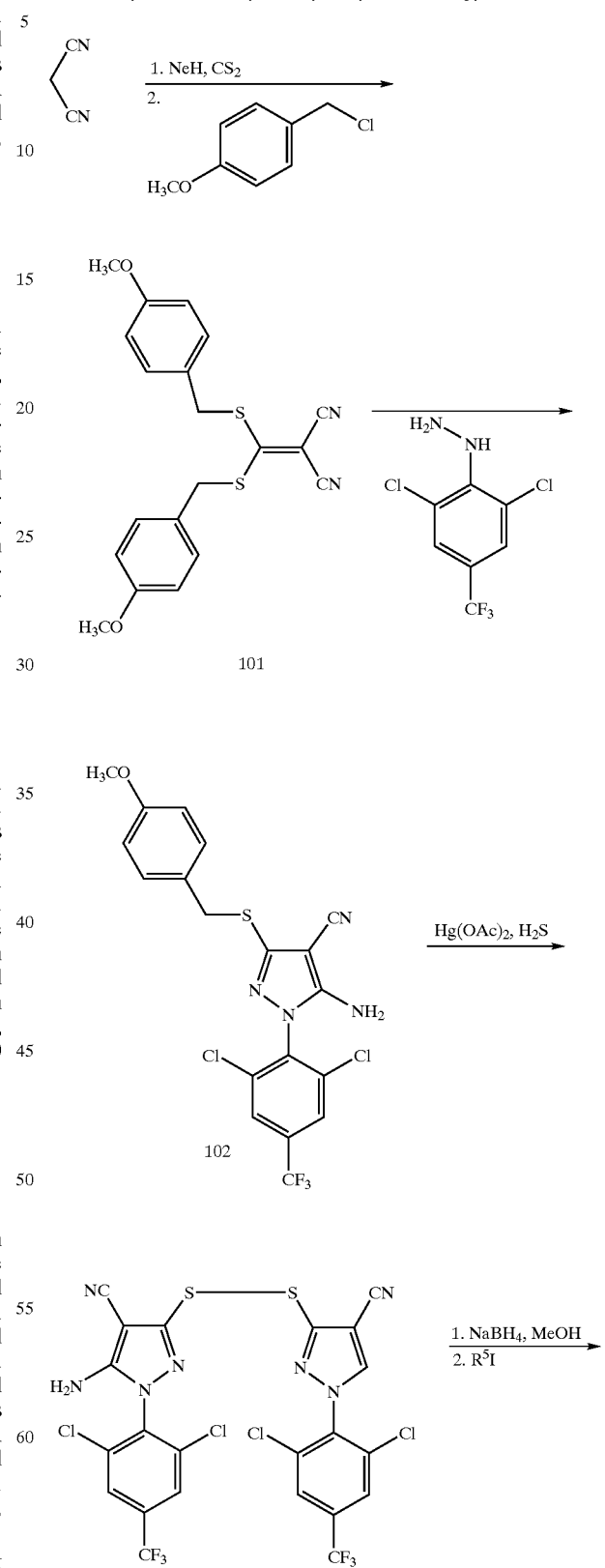

-continued

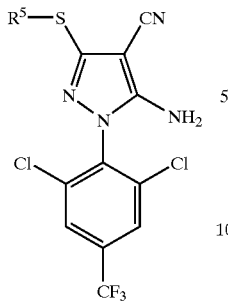

where $R^5$ is as defined above.

EXAMPLE 13

Alkylthioethers 12–17

{bis[(4-Methoxyphenyl)methylthio]
methylene}methane-1,1-dicarbonitrile (101)

DMF (40 mL) was slowly added to a rapidly stirred mixture of malononitrile (13.2 g, 0.2 mol) and NaH (9.6 g, 0.4 mol) and $CS_2$ (22.8 g, 0.3 mol) in benzene (200 mL). The reaction mixture was stirred at room temperature for 30 min and 4-methoxybenzyl chloride (93.6 g, 0.6 mol) was added. The resulting mixture was stirred for 12 h, and benzene (50 mL) and ice-water (200 mL) were added. The organic layer was separated, dried, and concentrated in vacuum. The product was purified by flash chromatography on silica gel, eluting with ethyl acetate:hexanes (15:85). Yield: 45.8 g (0.12 mol, 60%). NMR (δ, $CDCl_3$): 7.22 (4H, d, J=8.6 Hz); 6.85 (4H, d, J=8.6 Hz); 4.33 (4H, s); 3.79 (6H, s).

5-Amino-1-[2,6-dichloro-4-(trifluoromethyl)
phenyl]-3-[(4-methoxyphenyl)methylthio]pyrazole-4-carbonitrile (102)

A solution of 2,6-dichloro-4-trifluoromethyl phenyl hydrazine (245 mg, 1.0 mmol) and {bis[(4-methoxyphenyl) methylthio]methylene}methane-1,1-dicarbonitrile (101, 382 mg, 1.0 mmol) in isopropyl alcohol (15 mL) was heated at reflux for 16 h. The solvent was removed under reduced pressure and the desired product 102 obtained after chromatographic separation (silica gel) using ethyl acetate-hexanes (331 mg, 70%). NMR (δ, $CDCl_3$): 7.7 (2H, s); 7.2 (2H, d, J=8.7 Hz); 6.8 (2H, d, J=8.7 Hz); 4.41 (2H, broad); 4.23 (2H, s). MS: M+1=473 (calc.: 473).

5-Amino-3-({5-amino-1-[2,6-dichloro-4-(trifluoromethyl)phenyl]-4-cyanopyrazol-3-yl}disulfanyl)-1-[2,6-dichloro-4-(tifluoromethyl)
phenyl]pyrazole-4-carbonitrile (103)

Compound 102 (473 mg, 1.0 mmol) was dissolved in TFA (6.5 mL) containing anisole (0.2 mL) at 0° C., and $Hg(OAc)_2$ (383 mg, 1.2 mmol) was added. The resulting mixture was stirred at 0° C. for 30 min, and TFA was removed in vacuum. The residue was dried in high-vacuum and dissolved in ethanol. $H_2S$ (g) was bubbled through the solution for 30 min. The black precipitate was filtered through Celite (diatomaceous earth). The filtrate was concentrated, dissolved in methylene chloride, and thoroughly washed with $NaHCO_3$ (sat sol, 30 mL). The residue was dissolved in methanol (20 mL) and stirred under air for 24 h. The methanol was removed under reduced pressure, and the residue purified by flash chromatography (25% ethyl acetate-hexanes) to yield the desired disulfide (103, 229 mg, 65% yield). NMR (δ, $CDCl_3$): 7.75 (4H, s); 4.7, (4H, broad). MS: M+1=703 (calc.: 703).

EXAMPLE 14

5-Amino-1-[2,6-dichloro-4-(trifluoromethyl)
phenyl]-3-ethylthiopyrazole-4-carbonitrile (12)

A solution of disulfide 103 (20 mg, 0.03 mmol) in ethanol (5 mL) was treated with excess $NaBH_4$ (15 mg) at room temperature. After 10 min excess ethyl iodide (50 μL) was added at room temperature, and the mixture stirred at room temperature for 2 h. The reaction mixture was cooled down to 0° C. (ice-water bath) and unreacted $NaBH_4$ was destroyed by dropwise addition of HCl (10%). The mixture was neutralized and extracted with ethyl ether (3×10 mL). The organic fractions were combined and washed with brine, dried, and the solvent removed under reduced pressure. Column chromatography yielded pure compound 12 (13 mg, 57%). NMR (δ, $CDCl_3$): 7.7 (2H, s); 4.5, (2H, broad); 3.0 (2H, q, J=7.4 Hz); 1.3 (3H, t, J=7.4 Hz). MS: M+1=381 (calc.: 381).

Table 1 lists compounds of the invention having various substituents at the 3, 4 and 5 positions of the pyrazine ring that have been synthesized according to the procedure depicted in Schemes 1–3.

TABLE 1

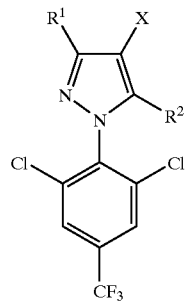

| Compound | $R^1$ | X | $R^2$ | MS [M + 1]+ |
|---|---|---|---|---|
| 1 | $SCH_3$ | H | H | 327 |
| 2 | $SCH_3$ | H | $NH_2$ | 342 |
| 3 | S(=O)$CH_3$ | H | H | 343 |
| 4 | S(=O)$_2CH_3$ | H | H | 359 |

TABLE 1-continued

[Structure: pyrazole with R¹ at 3-position, X at 4-position, R² at 5-position, N1 attached to 2,6-dichloro-4-(trifluoromethyl)phenyl]

| Compound | R¹ | X | R² | MS [M + 1]⁺ |
|---|---|---|---|---|
| 5 | SCH₃ | CN | NH₂ | 367 |
| 6 | S(=O)CH₃ | CN | NH₂ | 383 |
| 7 | S(=O)₂CH₃ | CN | NH₂ | 399 |
| 8 | SCH₃ | CN | H | 351 |
| 9 | S(=O)CH₃ | CN | H | 368 |
| 10 | S(=O)₂CH₃ | CN | H | 384 |
| 11 | OCH₃ | CN | NH₂ | 351 |
| 12 | SCH₂CH₃ | CN | NH₂ | 381 |
| 13 | SCH₂CH₂CH₃ | CN | NH₂ | 395 |
| 14 | SCH₂CF₃ | CN | NH₂ | 435 |
| 15 | SCH₂CH₂CF(CF3)₂ | CN | NH₂ | 549 |
| 16 | S-CH₂-cyclopropyl | CN | NH₂ | 407 |
| 17 | S-CH₂-(4-methoxyphenyl) | CN | NH₂ | 473 |
| 18 | SCH₃ | Cl | NH₂ | 376 |
| 19 | SCH₃ | Br | NH₂ | 420 |
| 20 | SCH₃ | I | NH₂ | 468 |
| 21 | SCH₃ | CO₂Et | NH₂ | 414 |
| 22 | S(=O)CH₃ | CO₂Et | NH₂ | 430 |
| 23 | S(=O)CH₃ | CO₂Et | H | 415 |
| 24 | S(=O)₂CH₃ | CO₂Et | NH₂ | 446 |
| 25 | S(=O)₂CH₃ | CO₂Et | H | 431 |
| 26 | SCH₃ | CO₂Me | NH₂ | 400 |
| 27 | SCH₃ | CO₂H | NH₂ | 386 |
| 28 | SCH₃ | C≡CH | NH₂ | 366 |
| 28' | SCH₃ | C≡C—SiMe₃ | NH₂ | 470 |
| 29 | SCH₃ | C(=NOH)NH₂ | NH₂ | 400 |
| 30 | SCH₃ | 3-methyl-1,2,4-oxadiazol-5-yl | NH₂ | 424 |
| 31 | SCH₃ | 3-methyl-1,2,4-oxadiazol-5-yl | H | 409 |
| 32 | SCH₃ | thiophen-2-yl | NH₂ | 424 |
| 33 | SCH₃ | thiophen-3-yl | NH₂ | 424 |

TABLE 1-continued
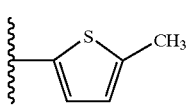
| Compound | R¹ | X | R² | MS [M + 1]⁺ |
| --- | --- | --- | --- | --- |
| 34 | SCH₃ | 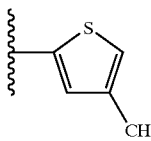 | NH₂ | 438 |
| 35 | SCH₃ | 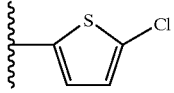 | NH₂ | 438 |
| 36 | SCH₃ | 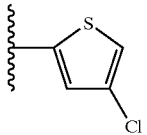 | NH₂ | 458 |
| 37 | SCH₃ | 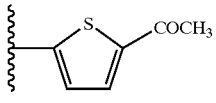 | NH₂ | 458 |
| 38 | SCH₃ | 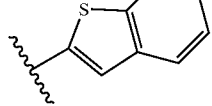 | NH₂ | 466 |
| 39 | SCH₃ | 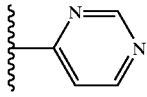 | NH₂ | 474 |
| 40 | SCH₃ | 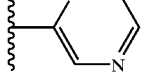 | NH₂ | 420 |
| 41 | SCH₃ | 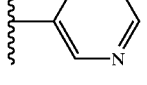 | NH₂ | 420 |
| 42 | SCH₃ | 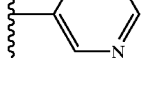 | H | 405 |
| 43 | S(O)CH₃ | 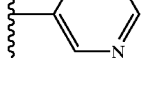 | H | 421 |

TABLE 1-continued

| Compound | R¹ | X | R² | MS [M + 1]⁺ |
|---|---|---|---|---|
| 44 | S(=O)₂CH₃ | pyrazine | H | 437 |
| 45 | SCH₃ | phenyl | NH₂ | 418 |
| 46 | SCH₃ | phenyl | H | 403 |
| 47 | SCH₃ | 2-methylphenyl | NH₂ | 432 |
| 48 | SCH₃ | 2-methylphenyl | H | 417 |
| 49 | SCH₃ | 2-fluorophenyl | NH₂ | 436 |
| 50 | SCH₃ | 2-chlorophenyl | NH₂ | 452 |
| 51 | SCH₃ | 2-(trifluoromethyl)phenyl | NH₂ | 486 |
| 52 | SCH₃ | 2-cyanophenyl | NH₂ | 443 |

TABLE 1-continued
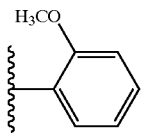
| Compound | R¹ | X | R² | MS [M + 1]⁺ |
|---|---|---|---|---|
| 53 | SCH₃ | 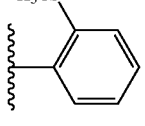 | NH₂ | 448 |
| 54 | SCH₃ | 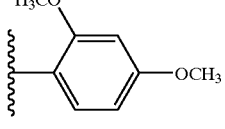 | NH₂ | 464 |
| 55 | SCH₃ | 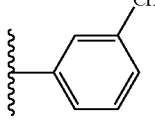 | NH₂ | 478 |
| 56 | SCH₃ | 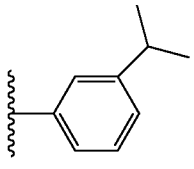 | NH₂ | 432 |
| 57 | SCH₃ | 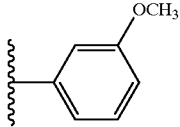 | NH₂ | 460 |
| 58 | SCH₃ | 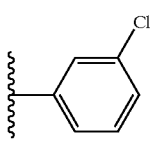 | NH₂ | 448 |
| 59 | SCH₃ | 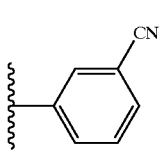 | NH₂ | 452 |
| 60 | SCH₃ | | NH₂ | 443 |

TABLE 1-continued

| Compound | R¹ | X | R² | MS [M + 1]⁺ |
|---|---|---|---|---|
| 61 | SCH₃ | 3-(CF₃)phenyl | NH₂ | 486 |
| 62 | SCH₃ | 3,5-bis(CF₃)phenyl | NH₂ | 554 |
| 63 | SCH₃ | 3-Cl-4-F-phenyl | NH₂ | 470 |
| 64 | SCH₃ | 3,4-di(OCH₃)phenyl | NH₂ | 478 |
| 65 | SCH₃ | 3,4,5-tri(OCH₃)phenyl | NH₂ | 508 |
| 66 | SCH₃ | 3,4-methylenedioxyphenyl | NH₂ | 462 |
| 67 | SCH₃ | 4-CH₃-phenyl | NH₂ | 432 |
| 68 | SCH₃ | 4-F-phenyl | NH₂ | 436 |

TABLE 1-continued

| Compound | R¹ | X | R² | MS [M + 1]⁺ |
|---|---|---|---|---|
| 69 | SCH₃ | 4-Cl-phenyl | NH₂ | 452 |
| 70 | SCH₃ | 4-Br-phenyl | NH₂ | 496 |
| 71 | SCH₃ | 4-CN-phenyl | NH₂ | 443 |
| 72 | SCH₃ | 4-CF₃-phenyl | NH₂ | 486 |
| 73 | SCH₃ | 4-phenyl-phenyl | NH₂ | 494 |
| 74 | SCH₃ | 4-isopropyl-phenyl | NH₂ | 460 |
| 75 | SCH₃ | 4-tert-butyl-phenyl | NH₂ | 474 |
| 76 | SCH₃ | 4-OCH₃-phenyl | NH₂ | 448 |
| 77 | SCH₃ | 4-OCH₃-phenyl | H | 433 |
| 78 | SCH₃ | 4-SCH₃-phenyl | NH₂ | 464 |
| 79 | SCH₃ | 4-OCF₃-phenyl | NH₂ | 502 |

Table 2 describes compounds of the invention having various substitution patterns on the 1-phenyl ring that have been formed according to the procedures depicted in Schemes 2 and 3.

TABLE 2

Compounds of general structure

| Compound | R7, R6, R5, R4, R3 | MS [M + 1] |
|---|---|---|
| 80 | H, H, H, H, H | 231 |
| 81 | Cl, H, H, H, Cl | 299 |
| 82 | Cl, H, H, H, H, | 266 |
| 83 | Cl, Cl, H, H, H | 299 |
| 84 | Cl, H, Cl, H, Cl | 335 |
| 85 | Cl, H, Cl, H, H | 299 |
| 86 | H, Cl, H, Cl, H | 299 |
| 87 | Cl, H, H, Cl, H | 299 |
| 88 | F, F, CF$_3$, F, F | 371 |
| 89 | F, F, CH$_3$, F, F | 317 |
| 90 | F, F, H, F, F | 303 |
| 91 | F, H, F, H, H | 285 |
| 92 | H, H, CF$_3$, H, H | 299 |
| 93 | F, F, F, F, F | 321 |
| 94 | H, CF$_3$, H, CF$_3$, H | 367 |
| 95 | H, H, Br, H, H | 310 |
| 96 | H, H, CH(CH$_3$)$_2$, H, H | 273 |
| 97 | H, Cl, Cl, H, H | 300 |
| 98 | H, H, OCF$_3$, H, H | 315 |
| 99 | H, CF$_3$, H, H, H | 299 |
| 100 | 3-Cl-5-CF$_3$-2-pyridyl | 335 |

EXAMPLE 15

In Vitro Assay to Screen Compounds for Ability to Bind Housefly GABA Receptors

Housefly neuronal membranes were prepared as described above from housefly heads. Test compounds were dissolved in dimethylsulfoxide (DMSO) at concentrations ranging from about 2 nM to about 100 mM. About 1 mL of a dissolved test compound was dispensed into a well of a 96-well polystyrene plate. About 100 mL of ice cold assay buffer (10 mM phosphate, 300 mM NaCl, pH 7.5) containing 5.2 nM 4'-Ethynyl-4-n-[2,3-$^3$H$_2$] propylbicycloorthobenzoate ($^3$H-EBOB, 38 Ci/mmol, available from NEN Life Science Products, Boston, Mass.) was added to the well, followed by about 100 mL of ice cold assay buffer containing about 0.5–1.0 mg/mL housefly neuronal membranes. Control wells were prepared the same way except that the housefly neuronal membranes were omitted from the "negative" wells, and the test compounds were omitted from the "positive" wells. The samples were incubated for about 45 min at about 24° C. and then filtered on a 0.1% (w/v) polyethylenimine-soaked glass fiber Filtermat A (available from EG&G Wallac Inc., Gaithersburg, Md.) followed by four 100 mL rinses of cold assay buffer using a Harvester 96® cell harvester (available from Tomtec, Orange, Conn.). The filtermat was air dried and radioactivity bound to the filtermat was detected with either a 1450 MicroBeta® Trilux scintillation counter (available from EG&G Wallac Inc.) or a Topcount NXT™ scintillation counter (available from Packard Instrument Co., Meriden, Conn.) using standard methods.

Specific binding was considered to be the difference between total $^3$H bound to the neuronal membranes in the absence of any inhibitors and nonspecific $^3$H bound to the neuronal membranes upon the addition of 5 mM unlabeled EBOB. The average radioactivity contained in the "negative" wells was subtracted from each of the assay wells. The results indicated that about 60–90% of the $^3$H-EBOB bound to the housefly neuronal membranes in the absence of inhibitors was specifically bound. Compounds that displaced $^3$H-EBOB at a level equivalent to 5 mM unlabeled EBOB were said to display "100% inhibition" of $^3$H-EBOB binding, while compounds that did not displace $^3$H-EBOB at all were said to display "0% inhibition" of $^3$H-EBOB binding. Compounds that displaced $^3$H-EBOB specifically bound to the housefly neuronal membranes were tested at 24–48 different final concentrations, varying from about 0.1 nM to about 125 mM, in order to determine the concentration at which 50% of the maximum inhibition due to the addition of that compound was observed (IC$_{50}$). This value was calculated by plotting the data on a log-linear plot and either dropping a line to the x-axis perpendicular to a line drawn to the y-axis at approximately 50% inhibition of $^3$H-EBOB binding, or by fitting the data to the formula I=XY/(X+Z), in which I is the percent inhibition of $^3$H-EBOB binding, X is the inhibitor concentration, Y is the maximum percent inhibition of $^3$H-EBOB binding observed, and Z is the calculated IC$_{50}$.

The results indicated that several of the compounds tested had IC$_{50}$ values ranging from about 8 nM to about 100 mM. Compounds with the most activity are 5 (IC$_{50}$=8 nM); 21 (25 nM); 51 (90 nM); 78 (52 nM); 12 (54 nM); 8 (90 nM); 47 (50 nM); 58 (26 nM); 41 (87 nM); 32 (90 nM); 36 (23 nM); and 26 (43 nM).

EXAMPLE 16

In Vitro Assay to Screen Compounds for Their Ability to Bind Mouse Brain GABA Receptors Mouse brain membranes were prepared as described above from dissected mouse brains. Test compounds were dissolved in dimethylsulfoxide (DMSO) at concentrations ranging from about 2 nM to about 100 mM. About 1 µL of a dissolved test compound was dispensed into a well of a 96-well polystyrene plate. About 100 µL of ice cold assay buffer (10 mM phosphate, 300 mM NaCl, pH 7.5) containing 5.2 nM 4'-Ethynyl-4-n-[2,3-$^3$H$_2$] propylbicycloorthobenzoate ($^3$H-EBOB, 38 Ci/mmol, available from NEN Life Science Products, Boston, Mass.) was added to the well, followed by about 100 µL of ice cold assay buffer containing about 0.25–0.5 mg/mL mouse brain membranes. Control wells were prepared the same way except that the mouse brain membranes were omitted from the "negative" wells, and the test compounds were omitted from the "positive" wells. The samples were incubated for about 45 min at about 24° C. and then filtered on a 0.1% (w/v) polyethylenimine-soaked glass fiber Filtermat A (available from EG&G Wallac Inc., Gaithersburg, Md.) followed by four 100 mL rinses of cold assay buffer using a Harvester 96® cell harvester (available from Tomtec, Orange, Conn.). The filtermat was air dried and radioactivity bound to the filtermat was detected with either a 1450 MicroBeta® Trilux scintillation counter (available from EG&G Wallac Inc.) or a Topcount NXT™ scintillation counter (available from Packard Instrument Co., Meriden, Conn.) using standard methods.

Specific binding was considered to be the difference between total $^3$H bound to the mouse brain membranes in the absence of any inhibitors and nonspecific $^3$H bound to the mouse brain membranes upon the addition of 5 μM unlabeled EBOB. The average radioactivity contained in the "negative" wells was subtracted from each of the assay wells. The results indicated that about 80–95% of the $^3$H-EBOB bound to the mouse brain membranes in the absence of inhibitors was specifically bound. Compounds that displaced $^3$H-EBOB at a level equivalent to 5 μM unlabeled EBOB were said to display "100% inhibition" of $^3$H-EBOB binding, while compounds that did not displace $^3$H-EBOB at all were said to display "0% inhibition" of $^3$H-EBOB binding. Compounds that displaced $^3$H-EBOB specifically bound to the mouse brain membranes were tested at 24–48 different final concentrations, varying from about 1 nM to about 125 μM, in order to determine the concentration at which 50% of the maximum inhibition due to the addition of that compound was observed (IC$_{50}$). This value was calculated by plotting the data on a log-linear plot and either dropping a line to the x-axis perpendicular to a line drawn to the y-axis at approximately 50% inhibition of $^3$H-EBOB binding, or by fitting the data to the formula I=XY/(X+Z), in which I is the percent inhibition of $^3$H-EBOB binding, X is the inhibitor concentration, Y is the maximum percent inhibition of $^3$H-EBOB binding observed, and Z is the calculated IC$_{50}$.

The results indicated that several of the compounds tested had IC$_{50}$ values ranging from about 1 to about 100 μM. These compounds were compounds 5, 21, 51, 79, 12, 8, 47, 58, 41, 32, 36 and 26.

EXAMPLE 17

In Vivo Housefly Assay

This example describes an in vivo assay to screen compounds for their ability to kill houseflies via contact. Newly emerged houseflies (*Musca domestica*, available from Rincon-Vitova Insectaries, Inc., Ventura, Calif.) were sedated with carbon dioxide gas, collected in 50 mL polypropylene conical tubes containing filter paper saturated with 10% (w/w) sucrose in water, and allowed to feed at room temperature for about 2–4 hours. Test compounds were dissolved in dimethylsulfoxide (DMSO) at concentrations ranging from about 0.05 mM to about 100 mM. About 1 μL of dissolved test compound and about 100 μL of isopropanol were dispensed into the bottom of a 9 mL screw-top glass test tube. Positive control test tubes were prepared in the same manner except that no test compounds were dissolved in the DMSO. Each test tube was rolled to coat the sides with the chemical solution, and allowed to air dry 24–48 hours. About 20 houseflies were sedated by refrigeration at 0–4° C. and transferred to each test tube. Each test tube was sealed with organdy cloth secured by an open top screw cap and laid horizontally in the dark. After about 24 hours, the healthy, moribund, and dead houseflies in each test tube were counted. The percentage of dead houseflies in each test tube was then calculated using the formula M=100(D-(FC/100))/(F-(FC/100)), in which M is the percentage of dead houseflies due to the addition of the test compound, D is the number of dead houseflies in the test tube, F is the total number of houseflies in the test tube, and C is the percentage of dead houseflies in the control test tubes.

Compounds of the invention that affected the survival of houseflies preferably cause 20–100% mortality or morbidity at 100 mM. Results for compounds of the invention appear in Table 3, column 2, below.

EXAMPLE 18

In Vivo Cat Flea Assay

This example describes an in vivo assay to screen compounds for their ability to kill cat fleas via contact.

Test compounds were dissolved in dimethylsulfoxide (DMSO) at concentrations ranging from about 0.05 mM to about 100 mM. About 1 μL of dissolved test compound was dispensed onto a 6 mm (diameter) GF/C filter disk (filter material available from Whatman Inc., Clifton, N.J.) in the bottom of a 4 mL screw-top glass vial and allowed to air dry 24–48 hours. Positive control vials were prepared in the same manner except that no test compounds were dissolved in the DMSO. About 20 newly emerged cat fleas (*Ctenocephalides felis*) were sedated by refrigeration at 0–4° C. and transferred to each vial. Each vial was sealed with a thin, perforated Teflon™ septum secured by an open top screw cap and held vertically in the dark. After about 24–30 hours, the healthy, moribund, and dead cat fleas in each vial were counted. The percentage of dead cat fleas in each vial was then calculated using the formula M=100(D-(FC/100))/(F-(FC/100)), in which M is the percentage of dead cat fleas due to the addition of the test compound, D is the number of dead cat fleas in the test vial, F is the total number of cat fleas in the test vial, and C is the percentage of dead cat fleas in the control vials.

Compounds of the invention that affected the survival of cat fleas preferably cause 20–100% mortality or morbidity at 100 mM. Results for compounds of the invention appear in Table 3, column 3, below.

TABLE 3

Contact Assay Percent Mortality, 100 mM Compound

| Compound No.* | % Mortality, Flies | % Mortality, Fleas |
| --- | --- | --- |
| 5 | 45 | 1.1 |
| 8 | 100 | 14.5 |
| 12 | 40.5 | 5.6 |
| 18 | 92.8 | 32.3 |
| 20 | 42.4 | 4.4 |
| 26 | 32 | 2.1 |
| 28' | 80.1 | 2.2 |
| 30 | 95.4 | 0 |
| 36 | 48.8 | 9.3 |
| 38 | 61.2 | 8.5 |
| 45 | 33.6 | 14.7 |
| 46 | 100 | 0 |
| 48 | 9.6 | 60.8 |
| 51 | 3.9 | 58.7 |
| 67 | 33.6 | 10.9 |

*Compound No. refers to the number in Table 1, supra

Having now fully described this invention, it will be understood to those of ordinary skill in the art that the same can be performed within a wide and equivalent range of conditions, formulations, and other parameters without affecting the scope of the invention or any embodiment thereof. All patents and publications cited herein are fully incorporated by reference herein in their entirety.

What is claimed is:

1. A method of inhibiting a arthropod GABA receptor, comprising contacting one or more arthropod GABA receptors with one or more compounds of Formula I:

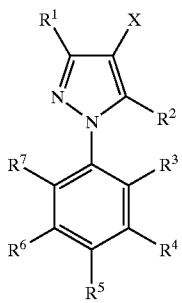

or a salt thereof, where

R$^1$ represents R$^5$O, R$^5$SO$_2$, R$^5$SO or R$^5$S in which R$^5$ is optionally halogen substituted C$_{1-6}$ alkyl, optionally halogen substituted C$_{2-6}$ alkenyl, optionally halogen substituted C$_{2-6}$ alkynyl, (C$_{3-7}$ cycloalkyl)methyl; or benzyl, optionally substituted by halo, hydroxy, methoxy or ethoxy;

X is halo, cyano, C$_{1-6}$ alkoxycarbonyl, C$_{2-6}$ alkynyl, optionally substituted C$_{6-14}$ aryl or an optionally substituted 5- to 7-membered heteroaromatic ring selected from the group consisting of pyridyl, thienyl, furanyl, isoxazolyl, thiazolyl, isothiazolyl, indolizinyl, isoindolyl, indolyl, indazolyl, quinolizinyl, quinolinyl, and isoquinolinyl, wherein said 5- to 7-membered heteroaromatic ring is linked via a ring carbon on said 5- to 7-membered heteroaromatic ring, and wherein said optional substituents are selected from the group consisting of C$_{1-4}$ alkyl, C$_{1-4}$ haloalkyl, halogen, C$_{1-4}$ alkoxy, C$_{1-4}$ haloalkoxy, C$_{1-4}$ alkoxycarbonyl, nitro, amino, cyano, C$_{1-4}$ alkylthio, C$_{1-4}$ alkylsulfinyl and C$_{1-4}$ alkylsulfonyl;

R$^2$ is hydrogen, amino, chloro, bromo, iodo, cyano, C$_{1-6}$ alkoxy, C$_{1-6}$ alkyl or C$_{6-10}$ aryl; and R$^3$–R$^7$ each represent hydrogen, halogen, straight- or branched-chain C$_{1-4}$ alkyl or C$_{1-4}$ alkoxy, either of which is unsubstituted or substituted by one or more halogen atoms, straight- or branched-chain C$_{1-4}$ alkylthio or C$_{1-4}$ alkylsulphinyl, either of which is substituted by one or more halogen atoms, nitro, cyano, or straight- or branched-chain C$_{1-4}$ alkylsulphonyl group which is unsubstituted or substituted by one or more halogen atoms.

2. A method for controlling arthropods, comprising contacting an animal, plant or object with a composition comprising (a) a pesticidally effective amount of at least one compound of Formula I:

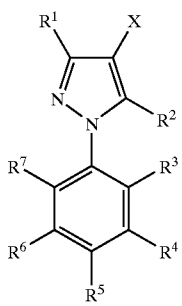

or a salt thereof, where

R$^1$ represents R$^5$O, R$^5$SO$_2$, R$^5$SO or R$^5$S in which R$^5$ is optionally halogen substituted C$_{1-6}$ alkyl, optionally halogen substituted C$_{2-6}$ alkenyl, optionally halogen substituted C$_{2-6}$ alkynyl, (C$_{3-7}$ cycloalkyl) methyl; or benzyl, optionally substituted by halo, hydroxy, methoxy or ethoxy;

X is halo, cyano, C$_{1-6}$ alkoxycarbonyl, C$_{2-6}$ alkynyl, optionally substituted C$_{6-14}$ aryl or an optionally substituted 5- to 7-membered heteroaromatic ring selected from the group consisting of pyridyl, thienyl, furanyl, isoxazolyl, thiazolyl, isothiazolyl, indolizinyl, isoindolyl, indolyl, indazolyl, quinolizinyl, quinolinyl, and isoquinolinyl, wherein said 5- to 7-membered heteroaromatic ring is linked via a ring carbon on said 5- to 7-membered heteroaromatic ring, and wherein said optional substituents are selected from the group consisting of C$_{1-4}$ alkyl, C$_{1-4}$ haloalkyl, halogen, C$_{1-4}$ alkoxy, C$_{1-4}$ haloalkoxy, C$_{1-4}$ alkoxycarbonyl, nitro, amino, cyano, C$_{1-4}$ alkylthio, C$_{1-4}$ alkylsulfinyl and C$_{1-4}$ alkylsulfonyl;

R$^2$ is hydrogen, amino, chloro, bromo, iodo, cyano, C$_{1-6}$ alkoxy, C$_{1-6}$ alkyl or C$_{6-10}$ aryl; and R$^3$–R$^7$ each represent hydrogen, halogen, straight- or branched-chain C$_{1-4}$ alkyl or C$_{1-4}$ alkoxy, either of which is unsubstituted or substituted by one or more halogen atoms, straight- or branched-chain C$_{1-4}$ alkylthio or C$_{1-4}$ alkylsulphinyl, either of which is substituted by one or more halogen atoms, nitro, cyano, or straight- or branched-chain C$_{1-4}$ alkylsulphonyl group which is unsubstituted or substituted by one or more halogen atoms; and (b) one or more pesticidally-acceptable diluents or carriers.

3. The method of claim 1 or claim 2, wherein R$^1$ is an C$_{1-4}$ alkylsulfonyl, C$_{1-4}$ alkylsulphinyl or C$_{1-4}$ alkylthio group, any of which is optionally halo-substituted.

4. The method of claim 1 or claim 2, wherein R$^1$ is —SCH$_3$, —SOCH$_3$, —SO$_2$CH$_3$, —SCH$_2$CH$_3$, —SCH$_2$CH$_2$CH$_3$, —SCH$_2$CF$_3$, cyclopropylmethylthio, 4-methoxybenzylthio, trifluoromethylthio or trifluoromethylsulfonyl.

5. The method of claim 4, wherein R$^1$ is —SCH$_3$.

6. The method of claim 1 or claim 2, wherein X is cyano, chloro, iodo, C$_{1-4}$ alkoxycarbonyl or C$_{2-4}$ alkynyl.

7. The method of claim 1 or claim 2, wherein X is phenyl, naphthyl, pyridyl, thienyl, furanyl, isoxazolyl, thiazolyl, isothiazolyl, indolizinyl, isoindolyl, indolyl, indazolyl, quinolizinyl, quinolinyl, or isoquinolinyl, any of which is optionally substituted by one or more substituents selected from the group consisting of C$_{1-4}$ alkyl, C$_{1-4}$ haloalkyl, halogen, C$_{1-4}$ alkoxy, C$_{1-4}$ haloalkoxy, C$_{1-4}$ alkoxycarbonyl, nitro, amino, cyano, C$_{1-4}$ alkylthio, C$_{1-4}$ alkylsulfinyl and C$_{1-4}$ alkylsulfonyl.

8. The method of claim 7, wherein X is 3-methyloxadiazin-5-yl, thiophen-2-yl; thiophen-3-yl, 5-methylthiophen-2-yl, 4-methylthiophen-2-yl, 5-chlorothiophen-2-yl, 4-chlorothiophen-2-yl, 5-methylcarbonylthiophen-2-yl, benzothiophen-2-yl, pyrimidin-6-yl, pyrazin-6-yl, phenyl, 2-methylphenyl, 2-fluorophenyl, 2-chlorophenyl, 2-trifluoromethylphenyl, 2-cyanophenyl, 2-methoxyphenyl, 2-methylthiophenyl, 2,4-dimethoxyphenyl, 3-methylphenyl, 3-isopropylphenyl, 3-methoxyphenyl, 2-fluorophenyl, 2-chlorophenyl, 2-trifluoromethylphenyl, 2-cyanophenyl, 2-methoxyphenyl, 2-methylthiophenyl, 3,5-di(trifluoromethyl)phenyl, 3-chloro-4-fluorophenyl, 3,4-dimethoxyphenyl, 3,4,5-trimethoxyphenyl, 1,3-benzodioxazol-5-yl, 4-methylphenyl, 4-fluorophenyl, 4-chlorophenyl, 4-bromophenyl, 4-trifluoromethylphenyl, 4-cyanophenyl, biphenyl, 4-isopropylphenyl, 4-methoxyphenyl, or 4-methylthiophenyl.

9. The method of claim 1 or claim 2, wherein $R^2$ is hydrogen.

10. The method of claim 1 or claim 2, wherein $R^2$ is $NH_2$.

11. The method of claim 1 or claim 2, wherein
$R^3$ is halogen;
$R^4$ is hydrogen;
$R^5$ is hydrogen, $C_{1-6}$ alkyl optionally substituted by one or more halogen atoms, $C_{1-6}$ alkoxy, optionally substituted by one or more halogen atoms;
$R_6$ is hydrogen; and
$R^7$ is halogen.

12. The method of claim 1 or claim 2, wherein
$R^3$, $R^5$ and $R^7$ are chloro; and $R^4$ and $R^6$ are hydrogen;
$R^3$ is chloro; $R^5$ is trifluoromethyl; and $R^4$, $R^7$, and $R^6$ are hydrogen;
$R^3$ is bromo; $R^5$ is trifluoromethyl; and $R^4$, $R^7$, and $R^6$ are hydrogen;
$R^3$ is bromo; $R^5$ and $R^7$ are trifluoromethyl; and $R^4$ and $R^6$ are hydrogen;
$R^3$ and $R^7$ are chloro; $R^5$ is trifluoromethyl; and $R^4$ and $R^6$ are hydrogen; or
$R^3$ and $R^7$ are bromo; $R^5$ is trifluoromethyl; and $R^4$ and $R^6$ are hydrogen.

13. The method of claim 1 or claim 2, wherein
$R^3$ and $R^7$ are chloro; $R^5$ is trifluoromethyl; and $R^4$ and $R^6$ are hydrogen; or
$R^3$ and $R^7$ are bromo; $R^5$ is trifluoromethoxy; and $R^4$ and $R^6$ are hydrogen.

14. The method of claim 1 or claim 2, wherein said compound is selected from the group consisting of:
1-[2,6-Dichloro-4-(trifluoromethyl)phenyl]-4-iodo-3-methylthiopyrazol-5-ylamine; 1-[2,6-Dichloro-4-(trifluoromethyl)phenyl]-4-chloro-3-methylthiopyrazol-5-ylamine;
1-[2,6-Dichloro-4-(trifluoromethyl)phenyl]-4-bromo-3-methylthiopyrazol-5-ylamine;
Methyl 5-amino-1-[2,6-dichloro-4-(trifluoromethyl)phenyl]-3-methylthiopyrazole-4-carboxylate;
5-Amino-1-[2,6-dichloro-4-(trifluoromethyl)phenyl]-3-methylthiopyrazole-4-carboxylic acid;
Ethyl 5-amino-1-[2,6-dichloro-4-(trifluoromethyl)phenyl]-3-methylthiopyrazole-4-carboxylate;
1-[2,6-Dichloro-4-(trifluoromethyl)phenyl]-4-(4-methylphenyl)-3-methylthiopyrazol-5-ylamine;
1-[2,6-Dichloro-4-(trifluoromethyl)phenyl]-4-phenyl-3-methylthiopyrazol-5-ylamine;
1-[2,6-Dichloro-4-(trifluoromethyl)phenyl]-4-phenyl-3-methylthiopyrazole;
1-[2,6-Dichloro-4-(trifluoromethyl)phenyl]-4-(2-methylphenyl)-3-methylthiopyrazol-5-ylamine;
1-[2,6-Dichloro-4-(trifluoromethyl)phenyl]-3-methylthio-4-[2-(trifluoromethyl)phenyl]pyrazol-5-ylamine;
1-[2,6-Dichloro-4-(trifluoromethyl)phenyl]-4-(2,4-dimethoxyphenyl)-3-methylthiopyrazol-5-ylamine;
1-[2,6-Dichloro-4-(trifluoromethyl)phenyl]-4-ethynyl-3-methylthiopyrazol-5-ylamine;
1-[2,6-Dichloro-4-(trifluoromethyl)phenyl]-4-(2-trimethylsilylethynyl)-3-methylthiopyrazol-5-ylamine;
1-[2,6-Dichloro-4-(trifluoromethyl)phenyl]-3-methylthio-4-pyrazin-2-ylpyrazol-5-ylamine;
1-[2,6-dichloro-4-(trifluoromethyl)phenyl]-3-methylthio-4-pyrazin-2-ylpyrazole;
1-[2,6-Dichloro-4-(trifluoromethyl)phenyl]-3-methylthio-4-(5-chlorothien-2-yl)pyrazol-5-ylamine;
1-[2,6-Dichloro-4-(trifluoromethyl)phenyl]-3-methylthio-4-(5-methoxycarbonylthien-2-yl)pyrazol-5-ylamine; and
1-[2,6-Dichloro-4-(trifluoromethyl)phenyl]-3-methylthio-4-(3-methyl-1,2,4-oxadiazin-5-yl)-2-ylpyrazol-5-ylamine;
5-Amino-1-[2,6-dichloro-4-(trifluoromethyl)phenyl]-3-methylthiopyrazole-4-carbonitrile;
1-[2,6-Dichloro-4-(trifluoromethyl)phenyl]-3-methylthiopyrazole-4-carbonitrile;
5-Amino-1-[2,6-dichloro-4-(trifluoromethyl)phenyl]-3-ethylthiopyrazole-4-carbonitrile;
5-Amino-3-methylthio-1-[2,3,5,6-tetrafluoro-4-(trifluoromethyl)phenyl]pyrazole-4-carbonitrile;
5-Amino-3-methylthio-1-[4-(trifluoromethyl)phenyl]pyrazole-4-carbonitrile;
5-Amino-1-[2,6-dichloro-4-(trifluoromethyl)phenyl]-3-(methylsulfinyl)pyrazole-4-carbonitrile;
5-Amino-1-[2,6-dichloro-4-(trifluoromethyl)phenyl]-3-(methylsulfonyl)pyrazole-4-carbonitrile;
1-[2,6-Dichloro-4-(trifluoromethyl)phenyl]-3-(methylsulfonyl)pyrazole-4-carbonitrile;
1-[2,6-Dichloro-4-(trifluoromethyl)phenyl]-3-(methylsulfinyl)pyrazole-4-carbonitrile;
5-amino-1-[2,6-dichloro-4-(trifluoromethyl)phenyl]-3-[(4-methoxyphenyl)methylthio]pyrazole-4-carbonitrile;
and pesticidally acceptable salts thereof.

15. A pesticidal composition comprising:
(a) a pesticidally effective amount of at least one compound of Formula I:

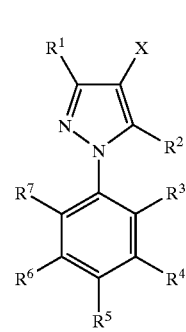

I or a salt thereof, where
$R^1$ represents $R^5O$, $R^5SO_2$, $R^5SO$ or $R^5S$ in which $R^5$ is optionally halogen substituted $C_{1-6}$ alkyl, optionally halogen substituted $C_{2-6}$ alkenyl, optionally halogen substituted $C_{2-6}$ alkynyl, $(C_{3-7}$ cycloalkyl) methyl; or benzyl, optionally substituted by halo, hydroxy, methoxy or ethoxy;
X is halo, cyano, $C_{1-6}$ alkoxycarbonyl, $C_{2-6}$ alkynyl, optionally substituted $C_{6-14}$ aryl or an optionally substituted 5- to 7-membered heteroaromatic ring selected from the group consisting of pyridyl, thienyl, furanyl, isoxazolyl, thiazolyl, isothiazolyl, indolizinyl, isoindolyl, indolyl, indazolyl, quinolizinyl, quinolinyl, and isoquinolinyl, wherein said 5- to 7-membered heteroaromatic ring is linked via a ring carbon on said 5- to 7-membered heteroaromatic ring, and wherein said optional substituents are selected from the group consisting of $C_{1-4}$ alkyl, $C_{1-4}$ haloalkyl, halogen, $C_{1-4}$ alkoxy, $C_{1-4}$ haloalkoxy, $C_{1-4}$ alkoxycarbonyl, nitro, amino, cyano, $C_{1-4}$ alkylthio, $C_{1-4}$ alkylsulfinyl and $C_{1-4}$ alkylsulfonyl;

$R^2$ is hydrogen, amino, chloro, bromo, iodo, cyano, $C_{1-6}$ alkoxy, $C_{1-6}$ alkyl or $C_{6-10}$ aryl; and $R^3$–$R^7$ each represent hydrogen, halogen, straight- or branched-chain $C_{1-4}$ alkyl or $C_{1-4}$ alkoxy, either of which is unsubstituted or substituted by one or more halogen atoms, straight- or branched-chain $C_{1-4}$ alkylthio or $C_{1-4}$ alkylsulphinyl, either of which is substituted by one or more halogen atoms, nitro, cyano, or straight- or branched-chain $C_{1-4}$ alkylsulphonyl group which is unsubstituted or substituted by one or more halogen atoms; and (b) one or more pesticidally-acceptable diluents or carriers.

16. The composition of claim 15, wherein $R^1$ is an $C_{1-4}$ alkylsulfonyl, $C_{1-4}$ alkylsulphinyl or $C_{1-4}$ alkylthio group, any of which is optionally halo-substituted.

17. The composition of claim 15, wherein $R^1$ is —$SCH_3$, —$SOCH_3$, —$SO_2CH_3$, —$SCH_2CH_3$, —$SCH_2CH_2CH_3$, —$SCH_2CF_3$, cyclopropylmethylthio, 4-methoxybenzylthio, trifluoromethylthio or trifluoromethylsulfonyl.

18. The composition of claim 15, wherein $R^1$ is —$SCH_3$.

19. The composition of claim 15, wherein X is cyano, chloro, iodo, $C_{1-4}$ alkoxycarbonyl or $C_{2-4}$ alkynyl.

20. The composition of claim 15, wherein X is phenyl, naphthyl, pyridyl, thienyl, furanyl, isoxazolyl, thiazolyl, isothiazolyl, indolizinyl, isoindolyl, indolyl, indazolyl, quinolizinyl, quinolinyl, or isoquinolinyl, any of which is optionally substituted by one or more substituents selected from the group consisting of $C_{1-4}$ alkyl, $C_{1-4}$ haloalkyl, halogen, $C_{1-4}$ alkoxy, $C_{1-4}$ haloalkoxy, $C_{1-4}$ alkoxycarbonyl, nitro, amino, cyano, $C_{1-4}$ alkylthio, $C_{1-4}$ alkylsulfinyl and $C_{1-4}$ alkylsulfonyl.

21. The composition of claim 15, wherein X is 3-methyloxadiazin-5-yl, thiophen-2-yl; thiophen-3-yl, 5-methylthiophen-2-yl, 4-methylthiophen-2-yl, 5-chlorothiophen-2-yl, 4-chlorothiophen-2-yl, 5-methylcarbonylthiophen-2-yl, benzothiophen-2-yl, pyrimidin-6-yl, pyrazin-6-yl, phenyl, 2-methylphenyl, 2-fluorophenyl, 2-chlorophenyl, 2-trifluoromethylphenyl, 2-cyanophenyl, 2-methoxyphenyl, 2-methylthiophenyl, 2,4-dimethoxyphenyl, 3-methylphenyl, 3-isopropylphenyl, 3-methoxyphenyl, 2-fluorophenyl, 2-chlorophenyl, 2-trifluoromethylphenyl, 2-cyanophenyl, 2-methoxyphenyl, 2-methylthiophenyl, 3,5-di(trifluoromethyl)phenyl, 3-chloro-4-fluorophenyl, 3,4-dimethoxyphenyl, 3,4,5-trimethoxyphenyl, 1,3-benzodioxazol-5-yl, 4-methylphenyl, 4-fluorophenyl, 4-chlorophenyl, 4-bromophenyl, 4-trifluoromethylphenyl, 4-cyanophenyl, biphenyl, 4-isopropylphenyl, 4-methoxyphenyl, or 4-methylthiophenyl.

22. The composition of claim 15, wherein $R^2$ is hydrogen.

23. The composition of claim 15, wherein $R^2$ is $NH_2$.

24. The composition of claim 15, wherein
$R^3$ is halogen;
$R^4$ is hydrogen;
$R^5$ is hydrogen, $C_{1-6}$ alkyl optionally substituted by one or more halogen atoms, $C_{1-6}$ alkoxy, optionally substituted by one or more halogen atoms;
$R_6$ is hydrogen; and
$R^7$ is halogen.

25. The composition of claim 15, wherein $R^3$ $R^5$ and $R^7$ are chloro; and $R^4$ and $R^6$ are hydrogen;

$R^3$ is chloro; $R^5$ is trifluoromethyl; and $R^4$, $R^7$, and $R^6$ are hydrogen;

$R^3$ is bromo; $R^5$ is trifluoromethyl; and $R^4$, $R^7$, and $R^6$ are hydrogen;

$R^3$ is bromo; $R^5$ and $R^7$ are trifluoromethyl; and $R^4$ and $R^6$ are hydrogen;

$R^3$ and $R^7$ are chloro; $R^5$ is trifluoromethyl; and $R^4$ and $R^6$ are hydrogen; or $R^3$ and $R^7$ are bromo; $R^5$ is trifluoromethyl; and $R^4$ and $R^6$ are hydrogen.

26. The composition of claim 15, wherein
$R^3$ and $R^7$ are chloro; $R^5$ is trifluoromethyl; and $R^4$ and $R^6$ are hydrogen;

or $R^3$ and $R^7$ are bromo; $R^5$ is trifluoromethoxy; and $R^4$ and $R^6$ are hydrogen.

27. The composition of claim 15, wherein said compound is selected from the group consisting of:

1-[2,6-Dichloro-4-(trifluoromethyl)phenyl]-4-iodo-3-methylthiopyrazol-5-ylamine; 1-[2,6-Dichloro-4-(trifluoromethyl)phenyl]-4-chloro-3-methylthiopyrazol-5-ylamine;

1-[2,6-Dichloro-4-(trifluoromethyl)phenyl]-4-bromo-3-methylthiopyrazol-5-ylamine;

Methyl 5-amino-1-[2,6-dichloro-4-(trifluoromethyl)phenyl]-3-methylthiopyrazole-4-carboxylate;

5-Amino-1-[2,6-dichloro-4-(trifluoromethyl)phenyl]-3-methylthiopyrazole-4-carboxylic acid;

Ethyl 5-amino-1-[2,6-dichloro-4-(trifluoromethyl)phenyl]-3-methylthiopyrazole-4-carboxylate;

1-[2,6-Dichloro-4-(trifluoromethyl)phenyl]-4-(4-methylphenyl)-3-methylthiopyrazol-5-ylamine;

1-[2,6-Dichloro-4-(trifluoromethyl)phenyl]-4-phenyl-3-methylthiopyrazol-5-ylamine;

1-[2,6-Dichloro-4-(trifluoromethyl)phenyl]-4-phenyl-3-methylthiopyrazole;

1-[2,6-Dichloro-4-(trifluoromethyl)phenyl]-4-(2-methylphenyl)-3-methylthiopyrazol-5-ylamine;

1-[2,6-Dichloro-4-(trifluoromethyl)phenyl]-3-methylthio-4-[2-(trifluoromethyl)phenyl]pyrazol-5-ylamine;

1-[2,6-Dichloro-4-(trifluoromethyl)phenyl]-4-(2,4-dimethoxyphenyl)-3-methylthiopyrazol-5-ylamine;

1-[2,6-Dichloro-4-(trifluoromethyl)phenyl]-4-ethynyl-3-methylthiopyrazol-5-ylamine;

1-[2,6-Dichloro-4-(trifluoromethyl)phenyl]-4-(2-trimethylsilylethynyl)-3-methylthiopyrazol-5-ylamine;

1-[2,6-Dichloro-4-(trifluoromethyl)phenyl]-3-methylthio-4-pyrazin-2-ylpyrazol-5-ylamine;

1-[2,6-dichloro-4-(trifluoromethyl)phenyl]-3-methylthio-4-pyrazin-2-ylpyrazole;

1-[2,6-Dichloro-4-(trifluoromethyl)phenyl]-3-methylthio-4-(5-chlorothien-2-yl)pyrazol-5-ylamine;

1-[2,6-Dichloro-4-(trifluoromethyl)phenyl]-3-methylthio-4-(5-methoxycarbonylthien-2-yl)pyrazol-5-ylamine; and 1-[2,6-Dichloro-4-(trifluoromethyl)phenyl]-3-methylthio-4-(3-methyl-1,2,4-oxadiazin-5-yl)-2-ylpyrazol-5-ylamine;

5-Amino-1-[2,6-dichloro-4-(trifluoromethyl)phenyl]-3-methylthiopyrazole-4-carbonitrile;

1-[2,6-Dichloro-4-(trifluoromethyl)phenyl]-3-methylthiopyrazole-4-carbonitrile;

5-Amino-1-[2,6-dichloro-4-(trifluoromethyl)phenyl]-3-ethylthiopyrazole-4-carbonitrile;

5-Amino-3-methylthio-1-[2,3,5,6-tetrafluoro-4-(trifluoromethyl)phenyl]pyrazole-4-carbonitrile;

5-Amino-3-methylthio-1-[4-(trifluoromethyl)phenyl]pyrazole-4-carbonitrile;

5-Amino-1-[2,6-dichloro-4-(trifluoromethyl)phenyl]-3-(methylsulfinyl)pyrazole-4-carbonitrile;

5-Amino-1-[2,6-dichloro-4-(trifluoromethyl)phenyl]-3-(methylsulfonyl)pyrazole-4-carbonitrile;

1-[2,6-Dichloro-4-(trifluoromethyl)phenyl]-3-(methylsulfonyl)pyrazole-4-carbonitrile;

1-[2,6-Dichloro-4-(trifluoromethyl)phenyl]-3-(methylsulfinyl)pyrazole-4-carbonitrile;

5-amino-1-[2,6-dichloro-4-(trifluoromethyl)phenyl]-3-[(4-methoxyphenyl)methylthio]pyrazole-4-carbonitrile;

and pesticidally acceptable salts thereof.

28. A compound of Formula I:

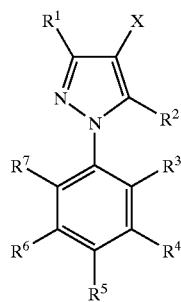

or a salt thereof, where $R^1$ represents $R^5O$, $R^5SO_2$, $R^5SO$ or $R^5S$ in which $R^5$ is optionally halogen substituted $C_{1-6}$ alkyl, optionally halogen substituted $C_{2-6}$ alkenyl, optionally halogen substituted $C_{2-6}$ alkynyl, $(C_{3-7}$ cycloalkyl)methyl; or benzyl, optionally substituted by halo, hydroxy, methoxy or ethoxy;

X is halo, $C_{1-6}$ alkoxycarbonyl, $C_{2-6}$ alkynyl, optionally substituted $C_{6-14}$ aryl or an optionally substituted 5- to 7-membered heteroaromatic ring selected from the group consisting of pyridyl, thienyl, furanyl, isoxazolyl, thiazolyl, isothiazolyl, indolizinyl, isoindolyl, indolyl, indazolyl, quinolizinyl, quinolinyl, and isoquinolinyl, wherein said 5- to 7-membered heteroaromatic ring is linked via a ring carbon on said 5- to 7-membered heteroaromatic ring, and wherein said optional substituents are selected from the group consisting of $C_{1-4}$ alkyl, $C_{1-4}$ haloalkyl, halogen, $C_{1-4}$ alkoxy, $C_{1-4}$ haloalkoxy, $C_{1-4}$ alkoxycarbonyl, nitro, amino, cyano, $C_{1-4}$ alkylthio, $C_{1-4}$ alkylsulfinyl and $C_{1-4}$ alkylsulfonyl;

$R^2$ is hydrogen, amino, chloro, bromo, iodo, cyano, $C_{1-6}$ alkoxy, $C_{1-6}$ alkyl or $C_{6-10}$ aryl; and $R^3$–$R^7$ each represent hydrogen, halogen, straight- or branched-chain $C_{1-4}$ alkyl or $C_{1-4}$ alkoxy, either of which is unsubstituted or substituted by one or more halogen atoms, straight- or branched-chain $C_{1-4}$ alkylthio or $C_{1-4}$ alkylsulphinyl, either of which is substituted by one or more halogen atoms, nitro, cyano, or straight- or branched-chain $C_{1-4}$ alkylsulphonyl group which is unsubstituted or substituted by one or more halogen atoms.

29. The compound of claim 28, wherein $R^1$ is an $C_{1-4}$ alkylsulfonyl, $C_{1-4}$ alkylsulphinyl or $C_{1-4}$ alkylthio group, any of which is optionally halo-substituted.

30. The compound of claim 28, wherein $R^1$ is —$SCH_3$, —$SOCH_3$, —$SO_2CH_3$, —$SCH_2CH_3$, —$SCH_2CH_2CH_3$, —$SCH_2CF_3$, cyclopropylmethylthio, 4-methoxybenzylthio, trifluoromethylthio or trifluoromethylsulfonyl.

31. The compound of claim 28, wherein $R^1$ is —$SCH_3$.

32. The compound of claim 28, wherein X is chloro or iodo.

33. The compound of claim 28, wherein X is $C_{1-4}$ alkoxycarbonyl or $C_{2-4}$ alkynyl.

34. The compound of claim 28, wherein X is phenyl, naphthyl, pyridyl, thienyl, furanyl, isoxazolyl, thiazolyl, isothiazolyl, indolizinyl, isoindolyl, indolyl, indazolyl, quinolizinyl, quinolinyl, or isoquinolinyl, any of which is optionally substituted by one or more substituents selected from the group consisting of $C_{1-4}$ alkyl, $C_{1-4}$ haloalkyl, halogen, $C_{1-4}$ alkoxy, $C_{1-4}$ haloalkoxy, $C_{1-4}$ alkoxycarbonyl, nitro, amino, cyano, $C_{1-4}$ alkylthio, $C_{1-4}$ alkylsulfinyl and $C_{1-4}$ alkylsulfonyl.

35. The compound of claim 28, wherein X is 3-methyloxadiazin-5-yl, thiophen-2-yl; thiophen-3-yl, 5-methylthiophen-2-yl, 4-methylthiophen-2-yl, 5-chlorothiophen-2-yl, 4-chlorothiophen-2-yl, 5-methylcarbonylthiophen2-yl, benzothiophen-2-yl, pyrimidin-6-yl, pyrazin-6-yl, phenyl, 2-methylphenyl, 2-fluorophenyl, 2-chlorophenyl, 2-trifluoromethylphenyl, 2-cyanophenyl, 2-methoxyphenyl, 2-methylthiophenyl, 2,4-dimethoxyphenyl, 3-methylphenyl, 3-isopropylphenyl, 3-methoxyphenyl, 2-fluorophenyl, 2-chlorophenyl, 2-trifluoromethylphenyl, 2-cyanophenyl, 2-methoxyphenyl, 2-methylthiophenyl, 3,5-di(trifluoromethyl)phenyl, 3-chloro-4-fluorophenyl, 3,4-dimethoxyphenyl, 3,4,5-trimethoxyphenyl, 1,3-benzodioxazol-5-yl, 4-methylphenyl, 4-fluorophenyl, 4-chlorophenyl, 4-bromophenyl, 4-trifluoromethylphenyl, 4-cyanophenyl, biphenyl, 4-isopropylphenyl, 4-methoxyphenyl, or 4-methylthiophenyl.

36. The compound of claim 28, wherein $R^2$ is hydrogen.

37. The compound of claim 28, wherein $R^2$ is $NH_2$.

38. The compound of claim 28, wherein:

$R^3$ is halogen;

$R^4$ is hydrogen;

$R^5$ is hydrogen, $C_{1-6}$ alkyl optionally substituted by one or more halogen atoms, $C_{1-6}$ alkoxy, optionally substituted by one or more halogen atoms;

$R_6$ is hydrogen; and $R^7$ is halogen, especially chloro.

39. The composition of claim 15, wherein $R^3$ $R^5$ and $R^7$ are chloro; and $R^4$ and $R^6$ are hydrogen;

$R^3$ is chloro; $R^5$ is trifluoromethyl; and $R^4$, $R^7$, and $R^6$ are hydrogen;

$R^3$ is bromo; $R^5$ is trifluoromethyl; and $R^4$, $R^7$, and $R^6$ are hydrogen;

$R^3$ is bromo; $R^5$ and $R^7$ are trifluoromethyl; and $R^4$ and $R^6$ are hydrogen;

$R^3$ and $R^7$ are chloro; $R^5$ is trifluoromethyl; and $R^4$ and $R^6$ are hydrogen; or $R^3$ and $R^7$ are bromo; $R^5$ is trifluoromethyl; and $R^4$ and $R^6$ are hydrogen.

40. The composition of claim 15, wherein $R^3$ and $R^7$ are chloro; $R^5$ is trifluoromethyl; and $R^4$ and $R^6$ are hydrogen; or $R^3$ and $R^7$ are bromo; $R^5$ is trifluoromethoxy; and $R^4$ and $R^6$ are hydrogen.

41. The composition of claim 15, wherein said compound is selected from the group consisting of:

1-[2,6-Dichloro-4-(trifluoromethyl)phenyl]-4-iodo-3-methylthiopyrazol-5-ylamine;

1-[2,6-Dichloro-4-(trifluoromethyl)phenyl]-4-chloro-3-methylthiopyrazol-5-ylamine;

1-[2,6-Dichloro-4-(trifluoromethyl)phenyl]-4-bromo-3-methylthiopyrazol-5-ylamine;

Methyl 5-amino-1-[2,6-dichloro-4-(trifluoromethyl)phenyl]-3-methylthiopyrazole-4-carboxylate;

5-Amino-1-[2,6-dichloro-4-(trifluoromethyl)phenyl]-3-methylthiopyrazole-4-carboxylic acid;

Ethyl 5-amino-1-[2,6-dichloro-4-(trifluoromethyl)phenyl]-3-methylthiopyrazole-4-carboxylate;

1-[2,6-Dichloro-4-(trifluoromethyl)phenyl]-4-(4-methylphenyl)-3-methylthiopyrazol-5-ylamine;

1-[2,6-Dichloro-4-(trifluoromethyl)phenyl]-4-phenyl-3-methylthiopyrazol-5-ylamine;

1-[2,6-Dichloro-4-(trifluoromethyl)phenyl]-4-phenyl-3-methylthiopyrazole;

1-[2,6-Dichloro-4-(trifluoromethyl)phenyl]-4-(2-methylphenyl)-3-methylthiopyrazol-5-ylamine;

1-[2,6-Dichloro-4-(trifluoromethyl)phenyl]-3-methylthio-4-[2-(trifluoromethyl)phenyl]pyrazol-5-ylamine;

1-[2,6-Dichloro-4-(trifluoromethyl)phenyl]-4-(2,4-dimethoxyphenyl)-3-methylthiopyrazol-5-ylamine;

1-[2,6-Dichloro-4-(trifluoromethyl)phenyl]-4-ethynyl-3-methylthiopyrazol-5-ylamine;

1-[2,6-Dichloro-4-(trifluoromethyl)phenyl]-4-(2-trimethylsilylethynyl)-3-methylthiopyrazol-5-ylamine;

1-[2,6-Dichloro-4-(trifluoromethyl)phenyl]-3-methylthio-4-pyrazin-2-ylpyrazol-5-ylamine;

1-[2,6-dichloro-4-(trifluoromethyl)phenyl]-3-methylthio-4-pyrazin-2-ylpyrazole;

1-[2,6-Dichloro-4-(trifluoromethyl)phenyl]-3-methylthio-4-(5-chlorothien-2-yl)pyrazol-5-ylamine;

1-[2,6-Dichloro-4-(trifluoromethyl)phenyl]-3-methylthio-4-(5-methoxycarbonylthien-2-yl)pyrazol-5-ylamine;

1-[2,6-Dichloro-4-(trifluoromethyl)phenyl]-3-methylthio-4-(3-methyl-1,2,4-oxadiazin-5-yl)-2-ylpyrazol-5-ylamine;

and pesticidally acceptable salts thereof.

\* \* \* \* \*